(12) United States Patent
Mullaney

(10) Patent No.: US 8,241,285 B2
(45) Date of Patent: Aug. 14, 2012

(54) METHOD AND CLAMPING APPARATUS FOR EXTERNAL FIXATION AND STABILIZATION

(75) Inventor: Michael W. Mullaney, Kinnelon, NJ (US)

(73) Assignee: ExtraOrtho, Inc., Memphis, TN (US)

(*) Notice: Subject to any disclaimer, the term of this patent is extended or adjusted under 35 U.S.C. 154(b) by 905 days.

(21) Appl. No.: 12/238,532

(22) Filed: Sep. 26, 2008

(65) Prior Publication Data

US 2009/0088751 A1  Apr. 2, 2009

Related U.S. Application Data

(60) Provisional application No. 60/995,535, filed on Sep. 27, 2007.

(51) Int. Cl.
  *A61F 5/04* (2006.01)
(52) U.S. Cl. .......................................... 606/59; 606/324
(58) Field of Classification Search .............. 606/54–59, 606/104, 250, 253, 277, 278, 324
  See application file for complete search history.

(56) References Cited

U.S. PATENT DOCUMENTS

| | | |
|---|---|---|
| 1,706,215 A | 3/1929 | Davidson |
| 2,705,603 A | 4/1955 | Bitz et al. |
| 3,044,512 A | 7/1962 | Jones |
| 3,154,331 A | 10/1964 | Engelhardt |
| 3,373,465 A | 3/1968 | Johnson et al. |
| 4,037,978 A | 7/1977 | Connelly |
| 4,115,966 A | 9/1978 | DeLee |
| 4,312,488 A | 1/1982 | Pierron |
| 4,483,334 A | 11/1984 | Murray |
| 4,620,533 A | 11/1986 | Mears |

(Continued)

FOREIGN PATENT DOCUMENTS

DE  2430234  1/1975

(Continued)

OTHER PUBLICATIONS

International Searching Authority/United States Patent Office, "Notification of Transmittal of the International Search Report and the Written Opinion of the International Searching Authority, or the Declaration," for PCT/US08/77800, mailed Dec. 2, 2008, 11 pages.

(Continued)

*Primary Examiner* — Eduardo C Robert
*Assistant Examiner* — Jerry Cumberledge
(74) *Attorney, Agent, or Firm* — Haynes and Boone, LLP

(57) ABSTRACT

Clamping devices and methods for external fixation systems include a post component having a yaw axis and a clamping system secured to the post component and rotatable about the yaw axis. The clamping system includes a outer jaw and a inner jaw having an inner surface facing the outer jaw. The outer and inner jaws together form an opening for receiving a fixation element of the external fixation system. The inner jaw and outer jaw have a roll axis alignable with a longitudinal axis of the fixation element. The clamping system and post component are rotatable about the roll axis. The inner jaw also includes a cylindrical outer-facing surface. The devices also include a base component having a cylindrical concave surface having a pitch axis. The concave surface of the base component interfaces with the cylindrical outer facing component on the inner jaw. The outer and inner jaws being rotatable relative to the base and the post component about the pitch axis.

41 Claims, 15 Drawing Sheets

U.S. PATENT DOCUMENTS

| | | | |
|---|---|---|---|
| 4,662,365 A | 5/1987 | Gotzen et al. | |
| 4,700,437 A | 10/1987 | Hoshino | |
| D295,725 S | 5/1988 | Shioda | |
| 4,817,897 A | 4/1989 | Kreusel | |
| 5,312,405 A | 5/1994 | Korotko et al. | |
| 5,427,465 A | 6/1995 | Sato | |
| 5,662,648 A | 9/1997 | Faccioli et al. | |
| 5,683,389 A | 11/1997 | Orsak | |
| 5,709,681 A | 1/1998 | Pennig | |
| 5,741,252 A | 4/1998 | Mazzio et al. | |
| 5,752,954 A | 5/1998 | Mata et al. | |
| 5,800,548 A | 9/1998 | Martin et al. | |
| 5,827,282 A | 10/1998 | Pennig | |
| 5,860,728 A | 1/1999 | Maglica | |
| 5,891,144 A | 4/1999 | Mata et al. | |
| 5,976,141 A | 11/1999 | Haag et al. | |
| 6,022,348 A | 2/2000 | Spitzer | |
| 6,080,153 A | 6/2000 | Mata et al. | |
| 6,102,911 A | 8/2000 | Faccioli et al. | |
| 6,217,577 B1 | 4/2001 | Hofmann | |
| 6,264,396 B1 * | 7/2001 | Dobrovolny | 403/391 |
| 6,376,775 B1 | 4/2002 | Leijon et al. | |
| 6,386,786 B1 | 5/2002 | Perlman et al. | |
| 6,409,729 B1 | 6/2002 | Martinelli | |
| 6,500,177 B1 | 12/2002 | Martinelli et al. | |
| 6,637,082 B1 | 10/2003 | Chang | |
| 6,652,523 B1 | 11/2003 | Evrard et al. | |
| 6,702,814 B2 * | 3/2004 | Walulik et al. | 606/57 |
| 6,716,212 B1 | 4/2004 | Pickens | |
| 6,736,775 B2 * | 5/2004 | Phillips | 600/234 |
| 7,048,735 B2 | 5/2006 | Ferrante et al. | |
| 7,241,071 B2 | 7/2007 | Carraher et al. | |
| 7,241,074 B2 * | 7/2007 | Thomke et al. | 403/385 |
| 7,261,713 B2 | 8/2007 | Langmaid | |
| 7,314,331 B1 | 1/2008 | Koros et al. | |
| 7,320,556 B2 | 1/2008 | Vagn-Erik | |
| 7,491,008 B2 * | 2/2009 | Thomke et al. | 403/373 |
| 7,527,626 B2 * | 5/2009 | Lutz et al. | 606/54 |
| 7,708,736 B2 | 5/2010 | Mullaney | |
| 7,931,650 B2 * | 4/2011 | Winquist et al. | 606/59 |
| 7,938,829 B2 | 5/2011 | Mullaney | |
| 2001/0004432 A1 * | 6/2001 | Pfister | 403/188 |
| 2002/0037193 A1 * | 3/2002 | Gibbons et al. | 403/344 |
| 2002/0042613 A1 | 4/2002 | Mata | |
| 2002/0061225 A1 | 5/2002 | Boucher et al. | |
| 2002/0165543 A1 | 11/2002 | Winquist et al. | |
| 2003/0149429 A1 * | 8/2003 | Ferrante et al. | 606/59 |
| 2004/0044344 A1 | 3/2004 | Winquist et al. | |
| 2005/0113831 A1 | 5/2005 | Franck et al. | |
| 2006/0039750 A1 | 2/2006 | Thomke | |
| 2006/0229602 A1 | 10/2006 | Olsen | |
| 2006/0229603 A1 | 10/2006 | Olsen | |
| 2006/0255521 A1 | 11/2006 | Brunner | |
| 2006/0287652 A1 | 12/2006 | Lessig et al. | |
| 2007/0038571 A1 | 2/2007 | Brown et al. | |
| 2007/0049932 A1 | 3/2007 | Richelsoph et al. | |
| 2007/0198012 A1 * | 8/2007 | Thomke et al. | 606/54 |
| 2008/0065068 A1 | 3/2008 | Thomke et al. | |
| 2009/0036891 A1 * | 2/2009 | Brown et al. | 606/57 |
| 2009/0299368 A1 | 12/2009 | Bauer | |

FOREIGN PATENT DOCUMENTS

| | | |
|---|---|---|
| EP | 1820461 | 8/2007 |
| WO | WO-89/05126 | 6/1989 |
| WO | WO9011055 | 10/1990 |
| WO | WO-92/12683 | 8/1992 |
| WO | WO-98/51227 | 11/1998 |
| WO | WO-99/25264 | 5/1999 |
| WO | WO-03/065911 | 8/2003 |

OTHER PUBLICATIONS

Swiss Patent Office, Application No. 03 891/90-6, titled "Fixateur externe," Applicant—Jaquet Orthopedie S.A., filed Dec. 16, 1991, 34 pages.

European Patent Office, International Search Report and Written Opinion dated Oct. 13, 2011, Application No. PCT/US2011/042813, 11 pages.

* cited by examiner

METHOD AND CLAMPING APPARATUS FOR EXTERNAL FIXATION AND STABILIZATION

CROSS-REFERENCE TO RELATED APPLICATIONS

This application claims the benefit of U.S. Provisional Application No. 60/995,535, entitled "Method and Apparatus for External Fixation and Stabilization," filed Sep. 27, 2007, the disclosure of which is incorporated herein by reference.

BACKGROUND

Proper stabilization and reduction of a fracture using an external fixation system requires proper alignment of the bone fragments. Such alignment requires a fixation component that securely joins the pins and wires to the bars, but that is readily adjustable. Conventional fixation components require a surgeon to clamp or lock the pins or wires to the bars, and if any adjustment is required during subsequent pin and bar placement, the surgeon must loosen the fixation component adjust it, and retighten the fixation component. This becomes tedious when complex fixation systems are required because surgeons spend inordinate amounts of time loosening, adjusting, and retightening fixation components. Further, such connections typically require two hands.

Some fixation components achieve mobility for ease of placement using joints connecting two clamps. Most systems only provide a revolute joint, the axis of which is perpendicular to both the pin and bar axes. Some systems replace the revolute joint with a ball joint allowing for roll pitch and yaw within some limited cone angle. This ball joint does come at an expense though, namely an increase in the pin to bar centerline distance which increases the working envelope and increases the moment arm subjecting the clamp device to increased moment loading necessitating a larger device.

The present invention overcomes one or more disadvantages of the prior art.

SUMMARY

In one exemplary aspect the present disclosure is directed to a clamping device for an external fixation system. The device includes, a first clamping system, a second clamping system, and a post component extending into the first and second clamping system. In some embodiments, the first clamping system includes a first outer jaw and a first inner jaw having an inner surface facing the outer jaw. The outer and inner jaws together forming an opening for receiving a first fixation element of the external fixation system. The first clamping system also includes a first base component having a concave surface interfacing with the first inner jaw and an opposing bottom facing surface. In some embodiments, the second clamping system includes a second outer jaw and a second inner jaw having an inner surface facing the second outer jaw. The second outer and second inner jaws together form a second opening for receiving a second fixation element of the external fixation system. The second clamping system includes a second base component having a concave surface interfacing with the second inner jaw and an opposing bottom facing surface. The concave surface of the first base component faces away from the concave surface of the second base component. The opposing bottom facing surface of the first component is in selective engagement with the opposing bottom facing surface of the second component. In some embodiments, the concave surface is a cylindrical surface.

In another exemplary aspect, the present disclosure is directed to a clamping device for an external fixation system. The device includes a post component having a yaw axis and a first clamping system secured to the post component and rotatable about the yaw axis. The first clamping system includes a first outer jaw and a first inner jaw having an inner surface facing the outer jaw. The outer and inner jaws together form an opening for receiving a first fixation element of the external fixation system. The first inner jaw and first outer jaw have a roll axis alignable with a longitudinal axis of the fixation element. The clamping system and post component are rotatable about the roll axis. The first inner jaw also has a cylindrical outer-facing surface. The device includes a first base component having a cylindrical concave surface having a pitch axis. The concave surface of the first base component interfaces with the cylindrical outer facing component on the inner jaw. The first outer and inner jaws are rotatable relative to the base and the post component about the pitch axis.

In another exemplary aspect, the present disclosure is directed to a method of building an external fixation system for stabilizing and reducing a bone. The method includes arranging a clamping device to be in an open bar-receiving condition by manually displacing a release element toward a rear portion of outer and inner jaw components of the clamping device. A fixation element is inserted into an opening between transverse grooves formed in the outer and inner jaw components. The release element is displaced toward a front end of the outer and inner jaws so that the release element applies loading to the outer jaw to rotate the outer jaw relative to the inner jaw and reduce the size of the opening between the transverse grooves formed in the outer and inner jaw components to place the clamping device in a provisionally locked state. The method also includes manipulating the clamping device relative to the fixation element. This includes pivoting the outer and inner jaws about an axis of a cylindrical concave surface on a base component, pivoting the clamping device about an axis of a post component extending through the clamping device, and rotating the clamping device about an axis of the fixation element. A locking element is tightened on the post component to compressively lock the outer and inner jaws in position relative to the post component and the base component.

DETAILED DESCRIPTION

Figure 1:
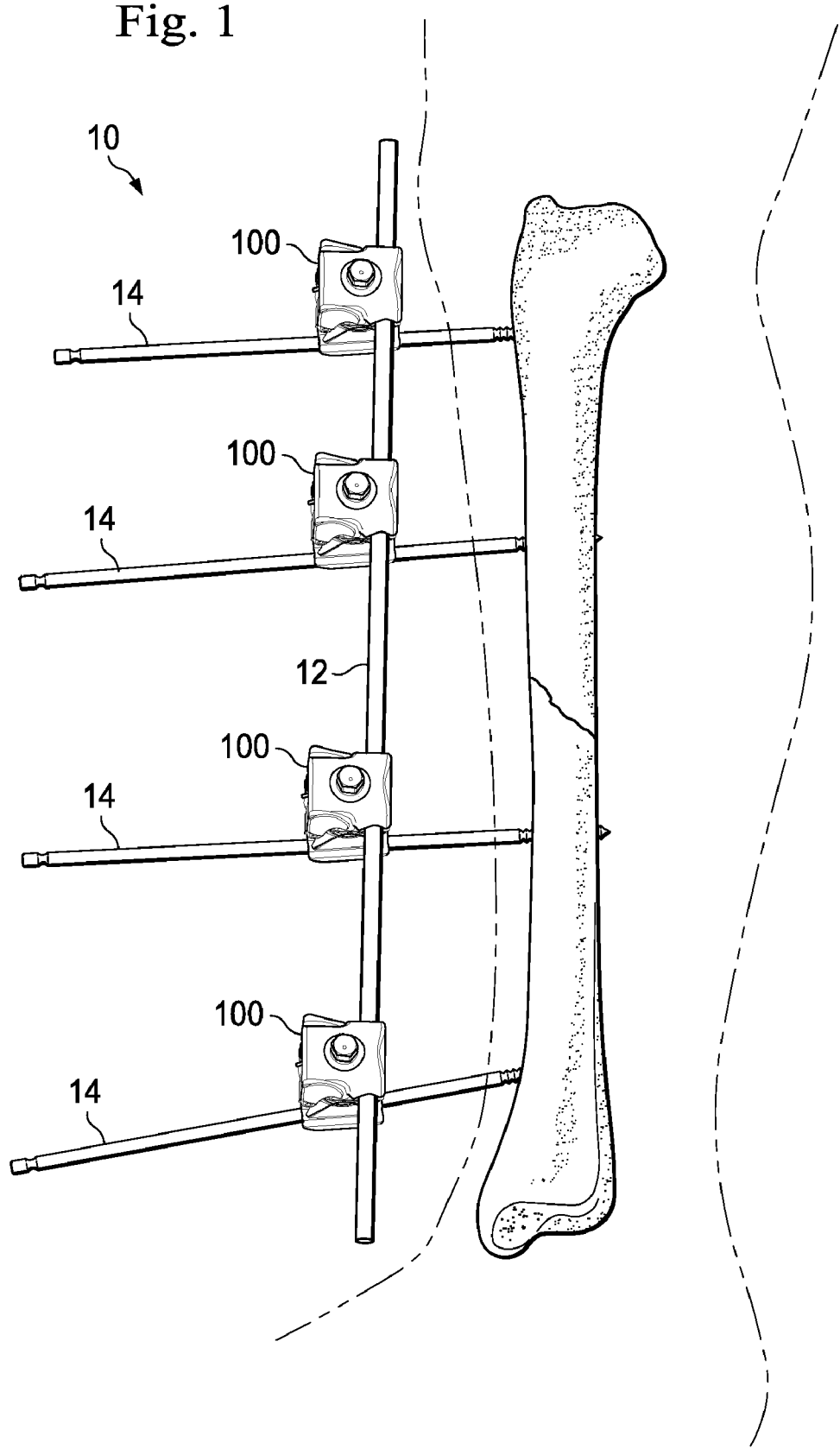
FIG. 1 is an illustration of an exemplary external fixation system according to one embodiment of the present disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The clamping systems disclosed herein combine desirable features of a relatively low profile with a high number of degrees of freedom. The embodiments shown each include two similar clamps connected by a binding post. Manipulation of the clamps permits relative movement in a roll, pitch, and yaw direction, all the while maintaining a relatively low profile.

In addition, some embodiments of the clamping systems operate through a range of three positions, including open, provisionally locked, and locked. The provisionally locked position connects the clamp to a bar or pin, but is still loose enough to permit post-placement manipulation. When the frame is in the desired arrangement, the clamp can be locked to resist further movement. In some embodiments, introducing the bar to the clamp triggers the clamp to move from the open position to the provisionally locked position. This enables surgeons to more easily assemble the external frame, and may permit one-hand provisional locking, both simplifying and speeding the frame orientation process.

FIG. 1 shows an external fixation system 10 attached to a patient's fractured tibia. The system 10 includes a rigid bar 12 and plurality of pins 14 drilled into the bone on opposing sides of the fracture. A clamping device 100 connects each pin 14 to the bar for rigid fixation and traction. Each pin 14 is received into a clamping device 100 by inserting the pin 114 between open top and bottom jaws of a fixator clamp of the clamping device 100. In some embodiments, inserting the pin 14 triggers the fixator clamp to change from an open position to a provisionally locked position about the pin 14. In this position, the fixator clamp can be rotated about the pin, be axially displaced along the pin, or may pitch about the up or down around the cylindrical axis of the base element, but the jaws maintain the pin in the clamp. Once the pins 14 are set, the bar 12 is introduced into another fixator clamp on the clamping device 100, forming a frame for the system. In some embodiments, as with the pins 14, inserting the bar 12 triggers the fixator clamp to change from an open position to a provisionally locked position. As remaining pins 14 are connected to the bar 12 using the clamping device 100, the fixation components may be adjusted to provide angulation and orientation necessary to align the bone for healing. Additional bar-to-bar fixation components and/or bar-to-pin fixation components may be added to expand and connect the frame as required. Once properly created, the frame may be locked by changing the clamp from the provisionally locked condition to the locked condition.

Figure 2:
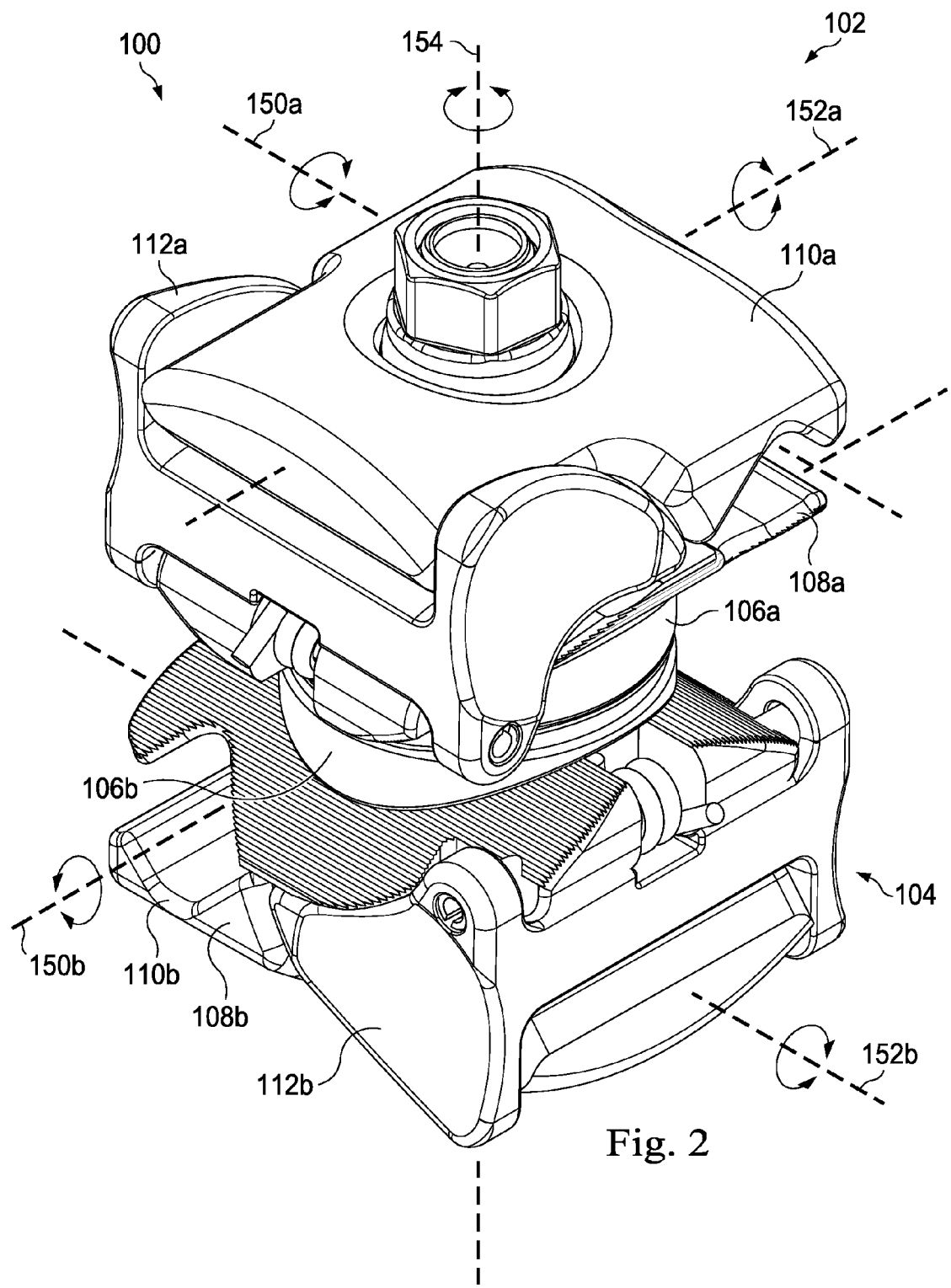
FIG. 2 is an illustration of a perspective view of a clamping device according to one exemplary embodiment of the present disclosure.
Figure 3:
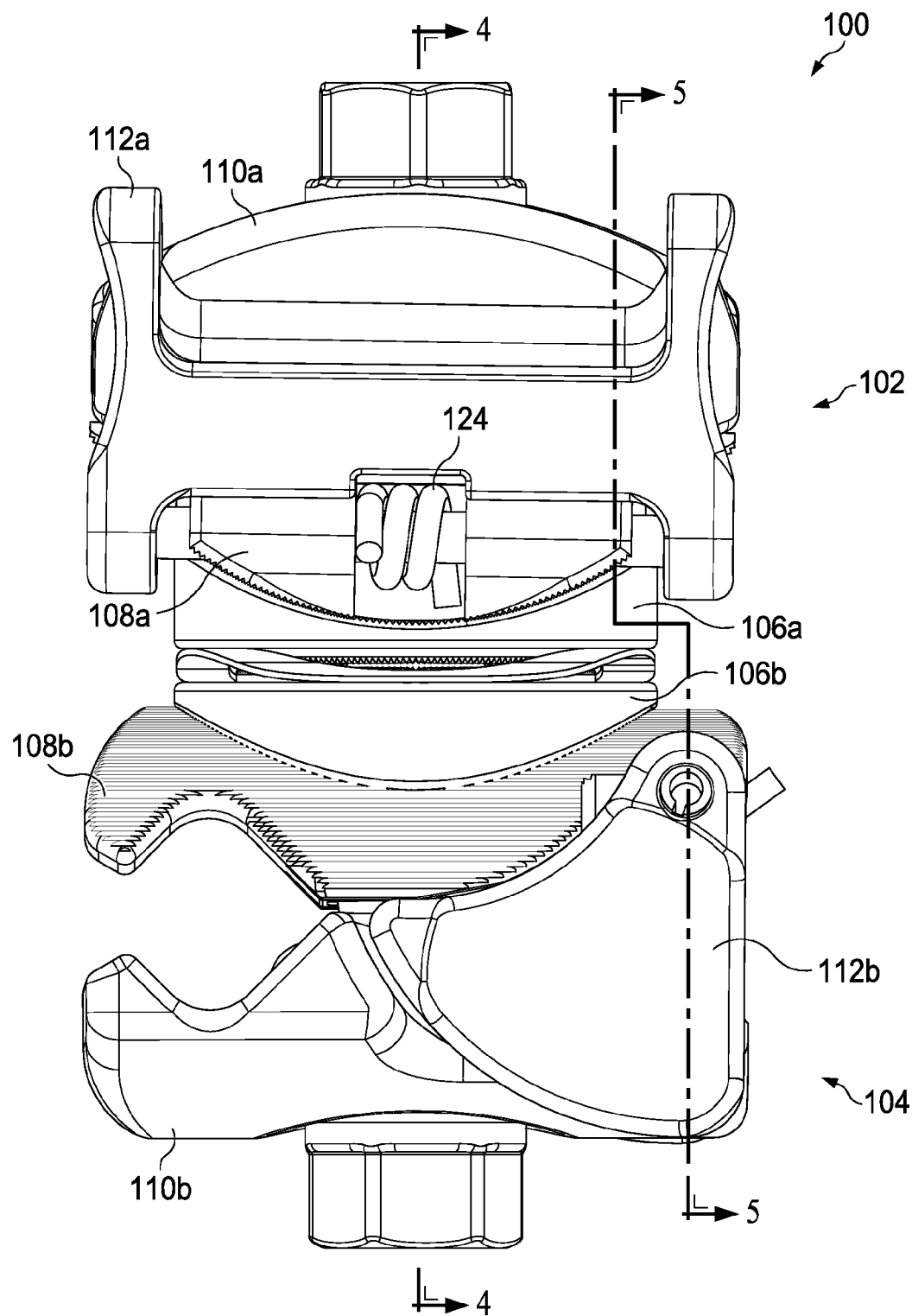
FIG. 3 is an illustration of a side view of the clamping device according to the exemplary embodiment in FIG. 2.

FIGS. 2 and 3 show an exemplary embodiment of a clamping device 100 according to one aspect of the present disclosure. The clamping device 100 includes a top fixator clamp 102 connected to a bottom fixator clamp 104. Each fixator clamp independently receives and secures a bar or pin, or alternatively, can be used to fixate bars to bars. In other embodiments, a single clamp can be used to fixate either a pin or a bar to some other apparatus such as a ring or monolateral external fixation and/or deformity correction device. The clamp mechanism whether used singly or in pairs operates the same as each half is independent of one another. In some embodiments, the clamps are substantially identical, while in other embodiments, the clamps are substantially similar, but have components sized or otherwise arranged to receive and secure different sized bars. In yet other embodiments, the clamping device 100 includes only a single clamp 102, 104, with an alternative arrangement in place of the other clamp 102, 104. Since bars and pins may be interchangeably held by either of the clamps 102, 104, as referred to herein, the use of the term bar is intended to mean any elongate structure, including rods, shafts, pins, wires or otherwise, that extend from bones to the clamping device 100 or from other bars to the clamping device 100.

For convenience in FIGS. 2-5, similar components are labeled with the same reference number, but are distinguished by a suffix, with the suffix "a" identifying components of the first or top clamp 102 and the suffix "b" identifying components of the bottom or second clamp 104.

Referring now to FIG. 2, The clamps 102, 104 each include a saddle base 106, an inner jaw 108, and an outer jaw 110. A release lever 112 operates to open the clamps 102, 104 and provisionally lock the clamps 102, 104 upon receipt of a bar.

Each clamp 102, 104 of the clamping device 100 provides multiple degrees of freedom. FIG. 2 shows the degrees of freedom as a roll axis 150, a pitch axis 152, and a yaw axis 154 in the upper and lower clamps 102, 104. The roll axis 150 is the axis of a bar within the clamps and about which the clamping device 100 rotates. The pitch axis 152 is the axis about which the outer and inner jaws rotate relative to the saddle base 106 and relative to the opposing clamp. The yaw axis 154 is defined by a binding post (described below) and about which one of clamps 102, 104 can rotate relative to the other.

Figure 4:
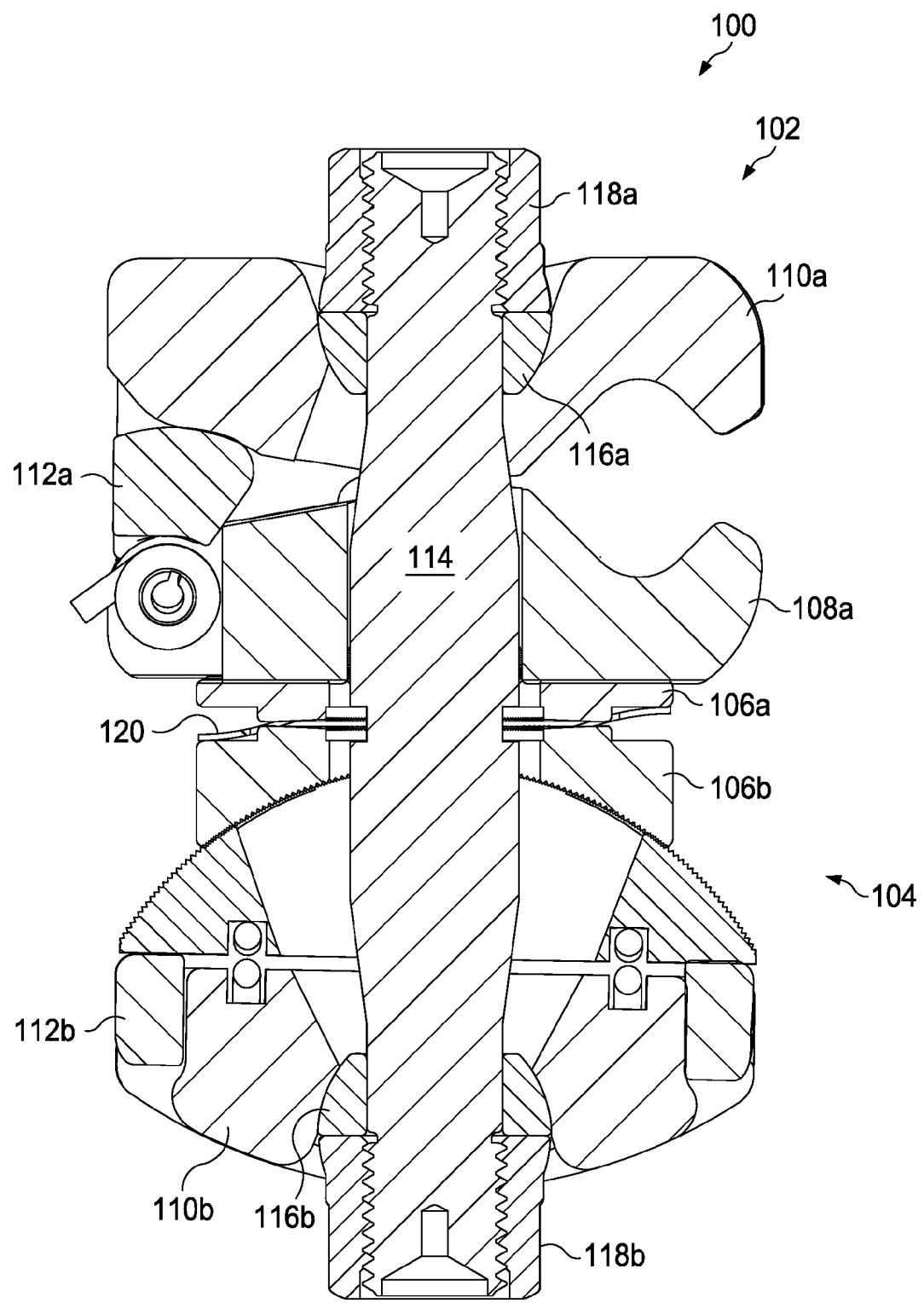
FIG. 4 is an illustration of a cross-sectional view along lines 4-4 in FIG. 3.
Figure 5:
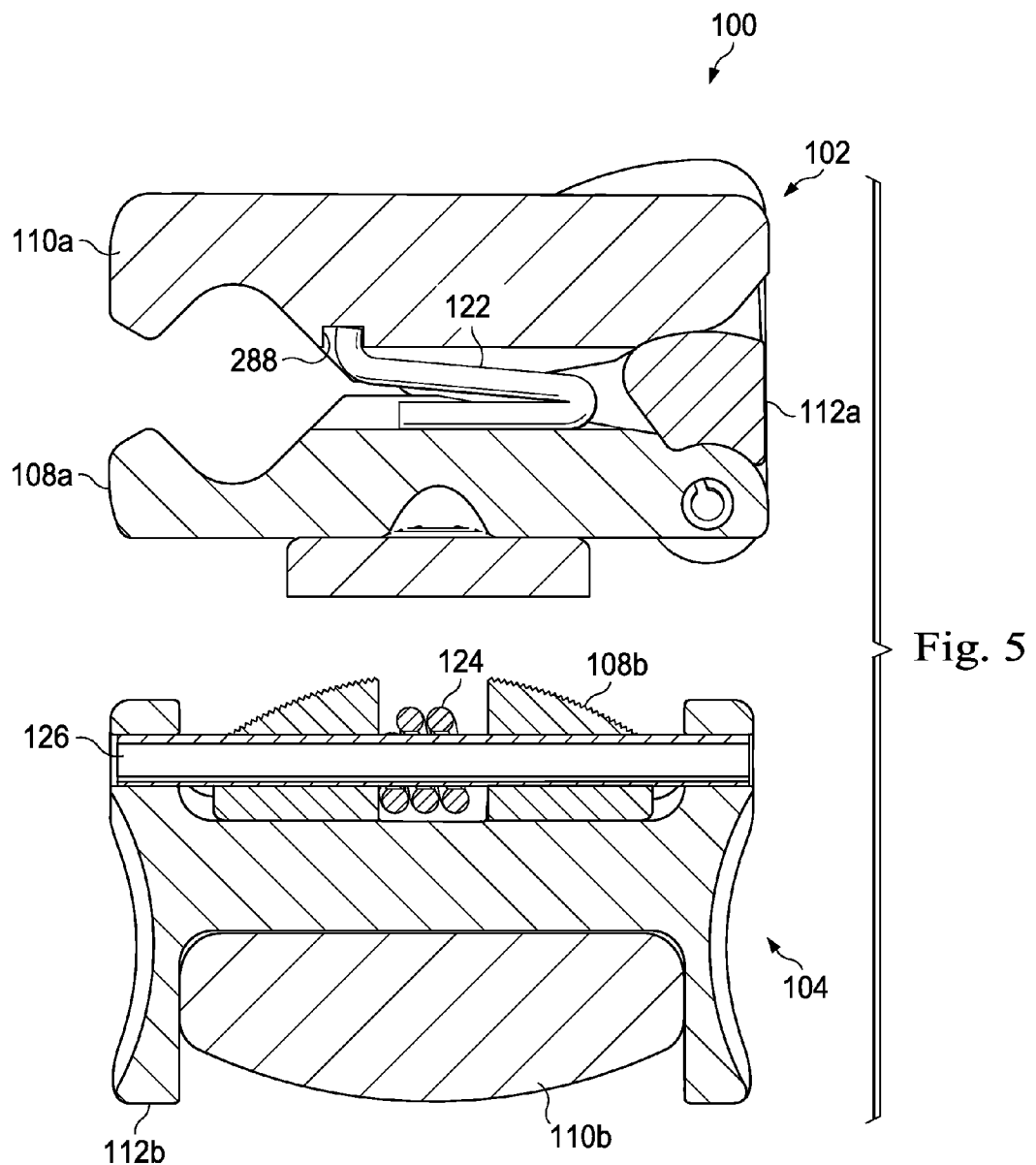
FIG. 5 is an illustration of a cross-sectional view along lines 5-5 in FIG. 3.

FIGS. 4 and 5 are cross-sectional views along lines 4-4 and 5-5 respectively showing inner features and components of the clamping device 100. Referring first to FIG. 4, the clamping device 100 includes a binding post 114 having spherical washers 116 and nuts 118 at each end. This binding post 114 passes through both the clamps 102, 104 and acts to hold the clamps together. Between the clamps 102, 104, a wave spring 120 provides a biasing force to space the clamps 102, 104 apart, enabling easy, independent rotation of the clamps 102, 104 about the binding post 114. This spring and its interaction with the saddle bases 106 of each of the clamps 102, 104 will be discussed further below.

Each clamp 102, 104 of the clamping device 100 includes biasing wire springs 120 (only one shown in FIG. 5), a torsion spring 124, and a pin 126 which pivotally connects the inner jaw 108 to the release lever 112. The biasing wire springs 122 lie between and interact with the inner and outer jaws 108, 110 of the clamp 102 to bias the jaws toward an open or bar-receiving position. The torsion spring 124 operates between the inner jaw 108 and the release lever 112 to bias the release lever 112 toward a locked position.

As will become apparent upon further reading, the release lever 112 may be rotated out of locking engagement with the outer jaw 110, at which time the wire spring 122 will bias the outer jaw 110 away from the inner jaw 108, thereby opening the jaws to receive a bar. When a bar is introduced between the outer and inner jaws 110, 108 with sufficient force, the bar displaces the outer jaw 110, which releases the release lever 112. The torsion spring 124 biases the release lever 112 into a locking engagement with the outer jaw 110, overcoming the biasing force of the wire spring 122, and forcing the outer jaw 110 to pivot toward the inner jaw 108 to provisionally lock or secure the bar between the inner and outer jaws 108, 110. In a provisionally locked state, a surgeon can still 1) rotate the clamping device 100 about the roll axis 150 or slide the clamping device 100 axially along the bar to further manipulate the bars to a desired position in a roll direction, 2) rotate the clamps 102, 104 of the clamping device 100 relative to each other about the yaw axis 154 and the binding post 114 in a yaw direction, and 3) rotate the inner jaw 108 of each clamp 102, 104 about the pitch axis 152 relative to the respective saddle base 106 to pivot the clamps 102, 104 in a pitch direction. Once the frame is in place, with the bars oriented in the desired directions, the surgeon can lock the clamping device 100 to the bars by tightening one or both nuts 118 on the binding post 114.

In other embodiments, a snap ring or other element or collar is secured at the center of the binding post 114 to allow for independent locking of either of clamps 102, 104. This snap ring allows for the locking of a single base element to the lower jaw and locking the jaw rather than locking both clamps at the same time. In some embodiments, the collar is an integral part of the binding post 114.

Figure 6A:
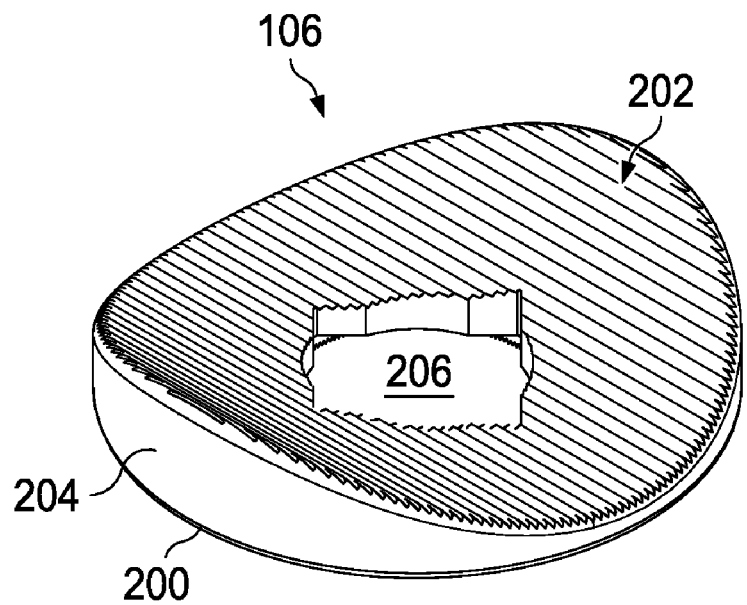
FIGS. 6A and 6B are illustrations of an exemplary saddle according to the exemplary embodiment of FIG. 2.
Figure 6B:
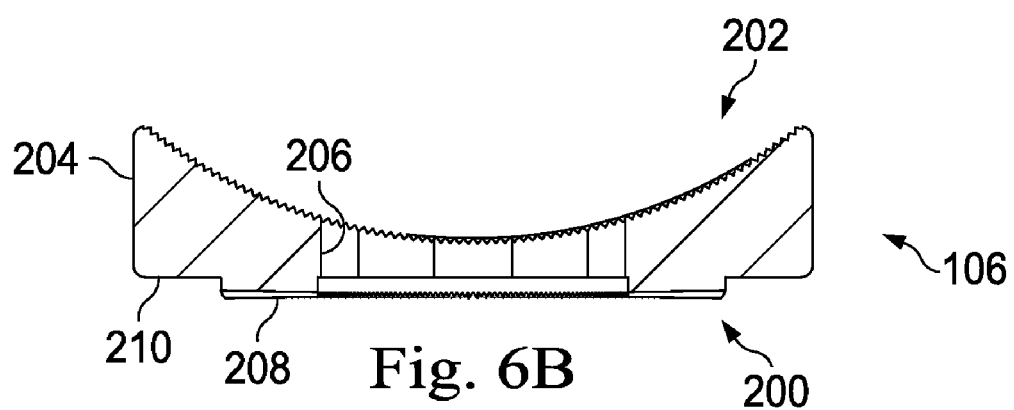

FIGS. 6A and 6B show an exemplary saddle base 106 of each clamp 102, 104. The saddle base includes an inner side 200, a concave outer-facing side 202, and a cylindrically shaped side wall 204 extending between the inner and outer-facing sides 200, 202. A central bore 206 extends through the saddle base 106 from the inner side 200 to the outer-facing side 202. This central bore 206 is sized to receive the binding post 114, as shown in FIG. 4, with enough clearance for the saddle base 106 to rotate about the binding post 114 and the yaw axis 154 to provide rotation in the yaw direction. In some embodiments, the central bore 206 is shaped to limit or restrict rotation about the binding post 114. For example, the binding post 114 may have a non-circular cross-section and the central bore 206 may be shaped to match the non-circular cross-section in a way that either limits or prohibits rotation about the binding post 114.

The inner side 200 includes a central circular-shaped surface 208 and a stepped shoulder 210. The central circular shaped surface 208 extends around the bore 206 and includes a circular array of radially extending splines that act to mate with the corresponding splines on the saddle base of the opposing clamp or on some other foundation if used without an opposing clamp. In some embodiments, the splines resemble those on a poker chip and provide positive retention from planar rotation when the faces are clamped together.

The stepped shoulder 210 on the inner side 200 extends about the central circular shaped surface 208 to the side wall 204 of the saddle base 106 and provides a seat for the wave spring 120 (FIG. 4). In use, and as shown in FIG. 4, the wave spring 120 interfaces with the stepped shoulder 210 of the saddle base 106 of each respective clamps 102, 104. The wave spring 120 biases the opposing shoulders 210 of each saddle base 106 apart, so that the radial splines on the opposing central circular shaped surfaces 208 are disengaged. Accordingly, the saddle bases 106, and therefore the clamps 102, 104, can rotate about the binding post 114 relative to each other. However, the wave spring 120 and the saddle shoulder 210 are sized so that upon tightening of the nut 118, the wave spring 120 can be compressed to lie along the shoulder 210 and the radial splines on the central circular shaped surfaces 208 of the opposing saddle bases 106 can engage to lock the clamps 102, 104 from pivoting relative to each other.

The concave outer-facing side 202 of saddle base 106 includes parallel, longitudinal splines configured to interdigitate with corresponding splines on the inner jaw 108. The concave outer-facing side 202 forms a radius about a saddle surface axis, about which the inner jaw 108 pivots as it interfaces with the saddle base 106. During this process, the saddle base 106 may displace relative to the inner jaw 108 against the wave spring 120 to alternatingly engage and disengage the splines, permitting the saddle base 106 or the inner jaw 108 to rotate relative to one another about the pitch axis 152 in FIG. 2. It should be noted that the angle of the longitudinal splines are such that they can be disengaged by radial displacement, and do not require longitudinal displacement to disengage due to any keystone effect.

FIGS. 7A-D show the inner jaw 108. The inner jaw 108, cooperating with the outer jaw 110, directly interfaces with the bar to secure the bar in place. The inner jaw 108 includes an inner clamp face 240 facing toward the outer jaw 110 and an outer clamp surface 241 that interfaces with the saddle base 106. The inner clamp face 240 includes a transverse groove 242 for receiving a bar, a main surface 244 having a central bore 246 and bias member grooves 248, and a pivot portion 250. The transverse groove 242 is located at a front end 249 of the inner jaw 108 and the pivot portion 250 lies at the opposite rear end 254 of the main surface 244.

Figure 7A:
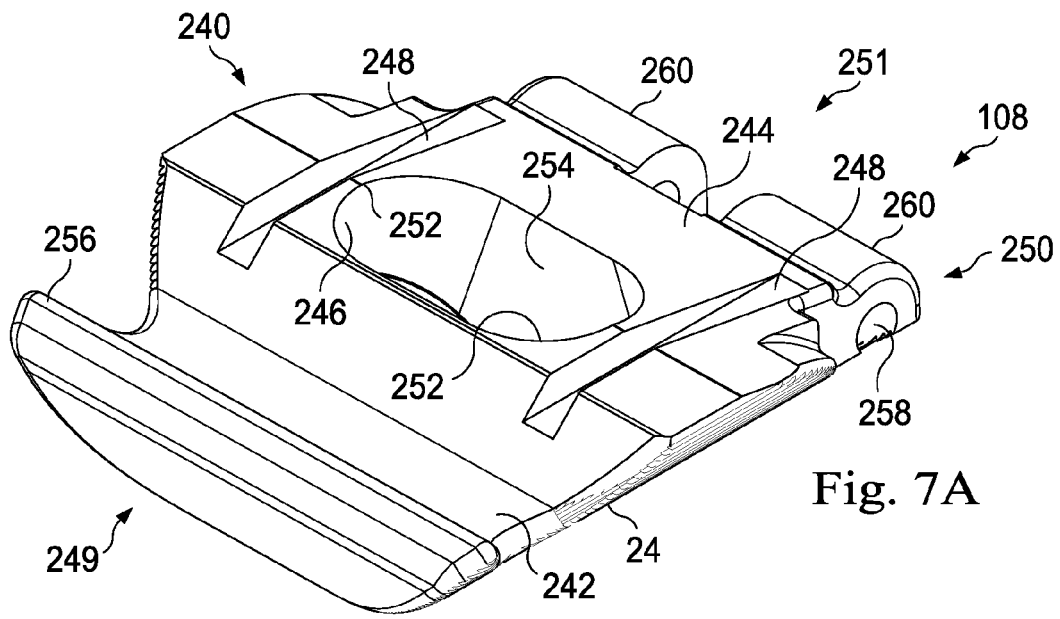
FIGS. 7A-D are illustrations of an exemplary inner jaw according to the exemplary embodiment of FIG. 2.
Figure 7B:
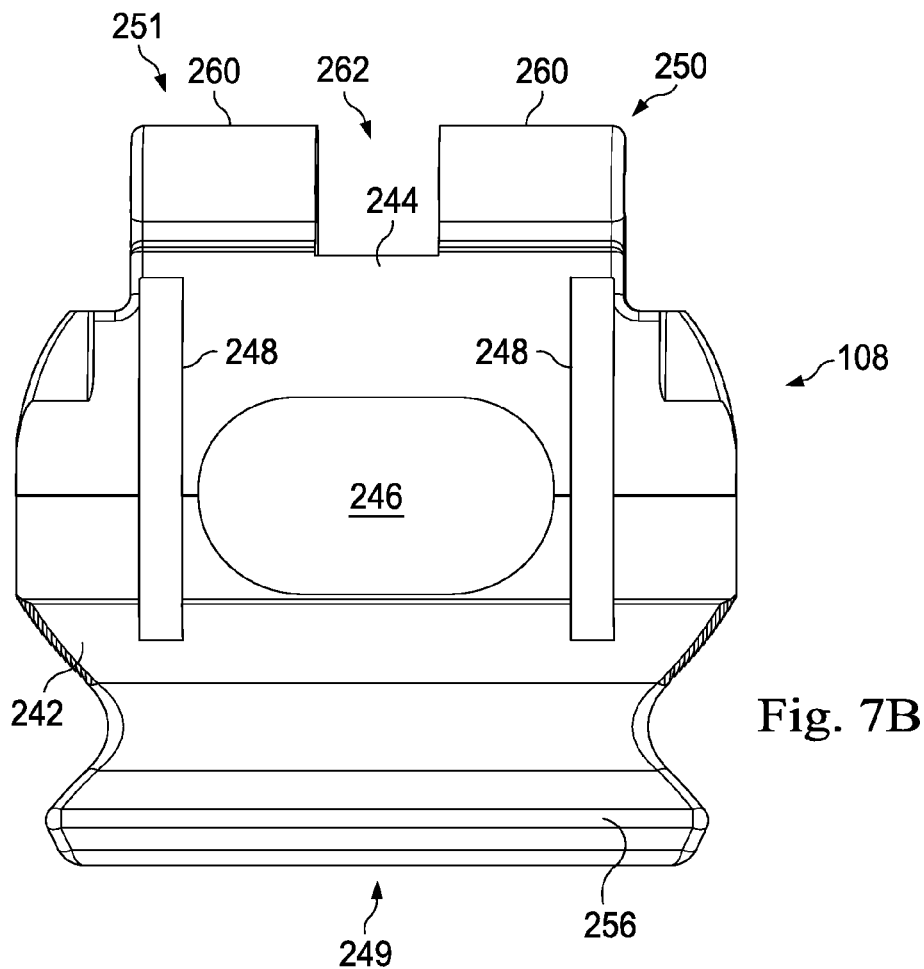

As shown in FIG. 7A, the transverse groove 242 extends from one lateral side to another and is shaped to receive a bar, pin, or other fixation or stabilization component. The transverse groove 242 is formed between a hook portion 256 at the front end of the clamp that secures a bar in the clamp. The transverse groove 242 may be formed with a rounded bottom portion or may be formed of a series of flats or faces. Some embodiments may have a combination of both curves and faces. The depth of the transverse groove 242 may vary between different clamps, such as the top clamp 102 and the bottom clamp 104, depending on the size of the bar intended to be gripped by the respective clamp. In some embodiments, the configuration and depth of the groove 242 may be configured to secure a smaller diameter bar, such as a bone pin or may be configured to secure a larger diameter bar, such as a frame bar. Further, in some embodiments, because the cross-section of the bars and pins may have shapes other than circular, the groove 242 may be shaped to also matingly interface with these bars and pins. For example, the groove 242 may include teeth, cut-outs, or other features that interface with bars having a non-smooth or non-circular outer surface.

Figure 7C:
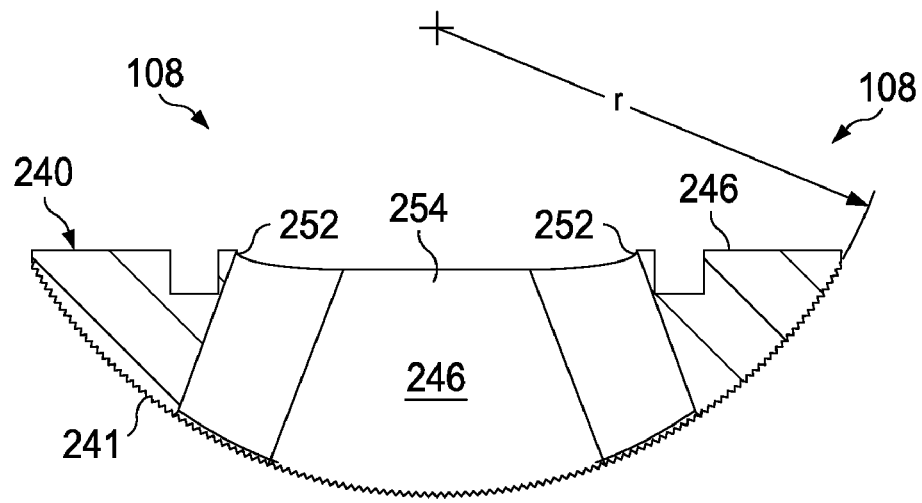

The central bore 246 is a transversely extending opening having a generally rectangular shape with a width and a length and the length being longer than the width. In the embodiment shown, the central bore 246 has rounded or arching ends separated by substantially parallel side edges spaced by the width. As best seen in FIG. 7C, the bore is cylindrical or conical-shaped at its ends 252 such that the bore length increases as the bore depth approaches the outer clamp surface 241. In contrast, bore sidewalls 254 are substantially parallel to each other, maintaining the bore width substantially constant. The binding post 114 fits within the central bore 246 as shown in FIG. 4, and provides only limited movement relative to the post 114 in the longitudinal, or width direction. However, because the bore length is greater than the bore width, the inner jaw 108 may move relative to the binding post 114 substantially more in the transverse, or length direction, to change the pitch of the inner jaw 108 relative to the post 114. This length is the result of a subtended arc who's vertex is coincident with the axis of the cylindrical surface ate ends 252.

This ultimately changes the pitch of the inner jaw 108 relative to the saddle base 106. In the embodiment shown, the inner jaw 108 pivots relative to the saddle base 20 degrees in each direction, giving a pivot range of 40 degrees. However, it should be apparent that in other embodiments, the range of pivot articulation may be greater or less than 40 degrees, and may be affected by the diameter of the binding post 114, the length of the central bore 246, as well as the angle of the bore ends 252.

In the embodiment shown, the two bias member grooves 248 in the main surface 244 extend from the transverse groove 242 rearwardly toward the pivot portion 250. These two bias member grooves 248 receive the wire springs 122 (FIG. 5) that operate to bias the inner jaw 108 and the outer jaw 110 to a closed position. The grooves 248 in the embodiment shown are parallel to each other, and have a decreasing depth from the transverse groove 242 toward the pivot portion 250, ultimately ending where the bias member grooves 248 meet the main surface 244.

Figure 7D:
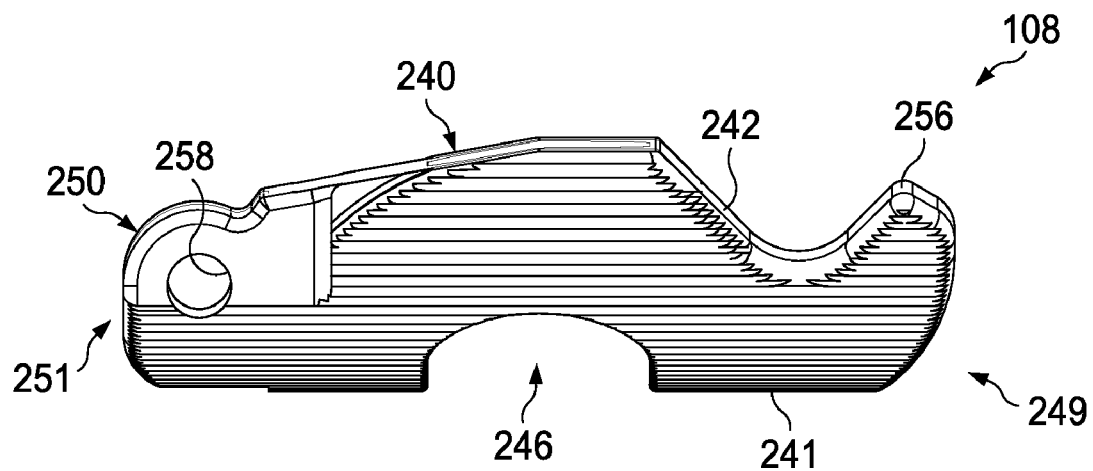

Referring to FIGS. 7A and 7D, the pivot portion 250 includes a cylindrical passage 258 that receives the pin 126 (FIG. 5) and cooperates with the release lever 112 in the form of a hinge. In this embodiment, the pivot portion 250 includes two connectors 260 separated by a centrally located gap 262. This gap 262 is sized to receive the torsion spring 124 (FIG. 5), as will be discussed further below.

The outer clamp surface 241 is a semi-cylindrical shaped surface that includes parallel, longitudinal splines shown in FIGS. 7C and 7D. These are configured to interdigitate with the corresponding splines on the saddle outer facing side 202 shown in FIG. 6B. The cylindrical shaped surface defines a radius r about which the inner jaw 108 pivots to provide the range of motion. Naturally, pivoting only occurs when the inner jaw 108 and the saddle base 106 are spaced so that the splines are not engaged. This may occur, for example, by displacing the saddle base towards the wave spring or in some embodiments.

FIGS. 8A-8D show the outer jaw 110 in greater detail. The outer jaw 110 includes a front end 272, a rear end 274, an inner clamp face 276, and an outer clamp surface 278. The inner clamp face 276 includes a bar-receiving transverse groove 280 adjacent the front end 272, a central bore 282, and bias member grooves 285. Similar to the groove 242 on the inner jaw 108 described above, the transverse groove 280 extends from one lateral side to another and is shaped to cooperate with the inner jaw 108 to receive a bar, pin or other fixation or stabilization component.

A hook portion 282 at the front end 272 defines a first portion of the transverse groove 280 and, as shown in the cross-section of FIG. 4, aligns with the inner jaw hook portion 256 to define an opening through which the bar may be introduced. Like the transverse groove 242 discussed above, the transverse groove 280 may be formed with a rounded bottom portion, flats, faces, or some combination of both. In some embodiments, the depth and shape of the groove 280 is the same as the depth and shape of the groove 248. Accordingly, the discussion above relating to the transverse groove 248 is equally applicable to the transverse groove 280.

Figure 8A:
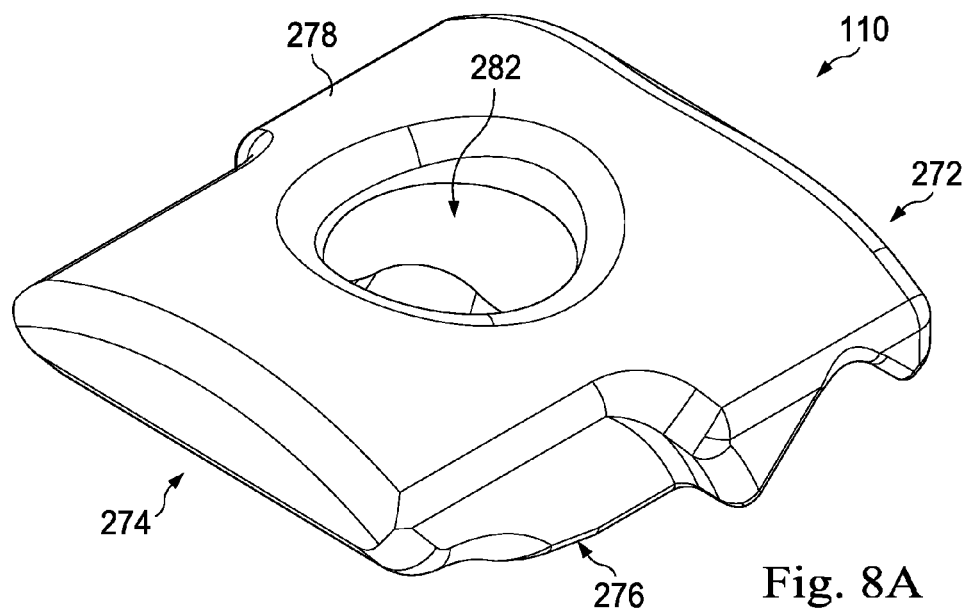
FIGS. 8A-D are illustrations of an exemplary outer jaw according to the exemplary embodiment of FIG. 2.

The central bore 282 includes features that enable it to provide articulation relative to the binding post 114 in a manner that the outer jaw articulation matches that of the inner jaw 108. FIGS. 8C and 8D show the outer jaw 110 in cross-section and, along with the views in FIGS. 8A and 8B, provide an indication of the multiple surface aspects of one exemplary central bore 282.

Figure 8B:
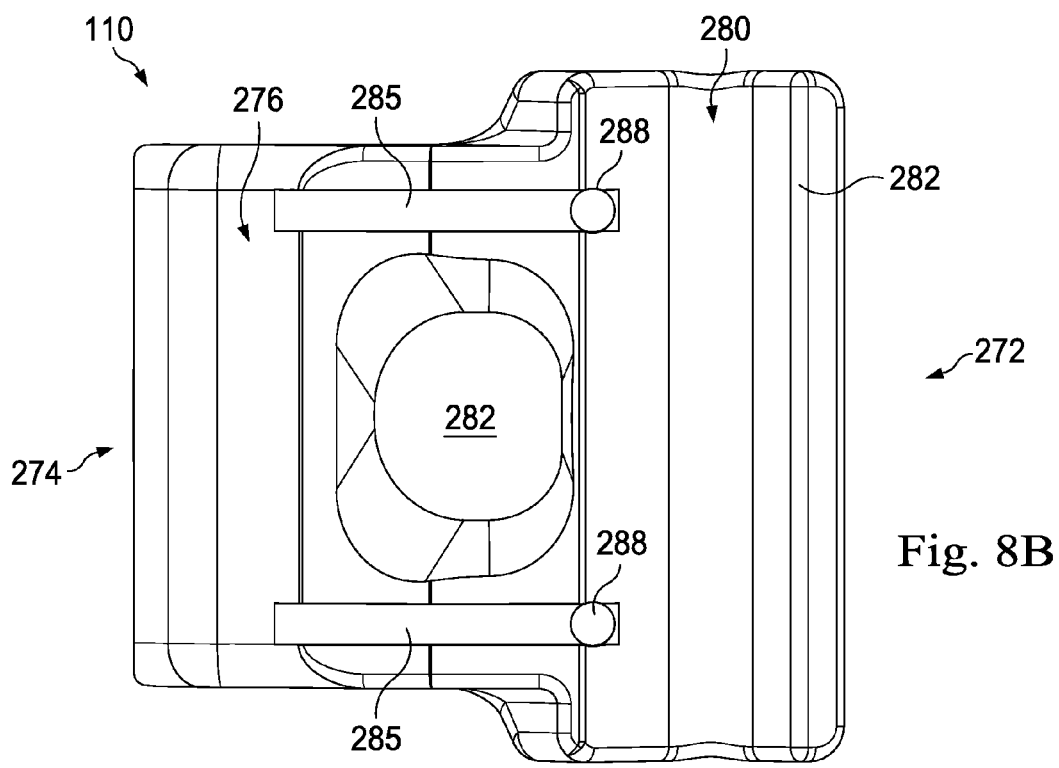
Figure 8C:
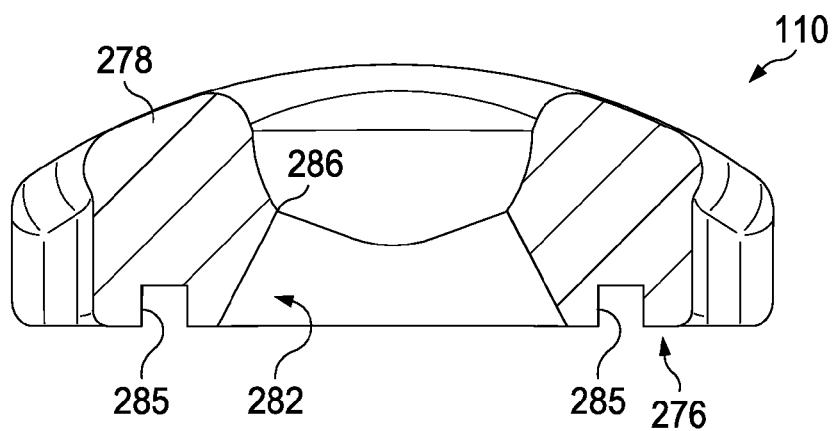
Figure 8D:
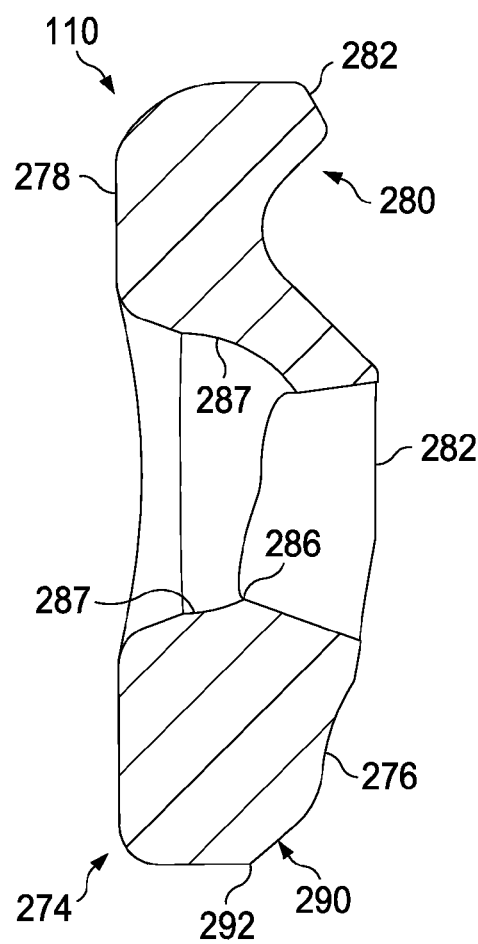

Referring to FIGS. 8B-D, the central bore 282 is generally hour-glass shaped, with a narrowing neck 286 located between the inner clamp face 276 and the outer clamp surface 278. At the inner clamp face 276, the central bore 282 is relatively rectangular shaped with a width and a length, the length being greater than the width. From the inner clamp face 276, the bore tapers inwardly toward the neck 286, with the inner bore surfaces including curved portions as well as planar portions. As discussed further below, the central bore portion between the neck 286 and the inner clamp face 276 is arranged and shaped to permit articulation relative to the binding post 114 in a manner to match articulation of the inner jaw 108 so that during articulation, the inner clamp face 276 of the outer jaw 110 faces the inner clamp face 240 of the inner jaw 108. Accordingly, in the embodiment shown the central bore 282 is sized to permit pivot rotation in the lateral direction of the outer jaw 110 within, for example, a pivot range of 40 degrees, matching that of the inner jaw 108. As discussed above, other pivot ranges are contemplated and considered to be within the scope of this disclosure. Unlike the exemplary inner jaw 108, however, the outer jaw 110 in this embodiment is configured to also provide articulation in the longitudinal direction or front-to-rear direction. Accordingly as shown in FIG. 8D, the longitudinal direction also includes side walls tapering from the neck toward the inner clamp face 276. These inner clamp faces are not symmetrically disposed, but permit more articulation in one longitudinal direction than the other. In the exemplary embodiment shown in FIG. 8D, for example, the inner clamp surface permits articulation from a center point in one direction of twenty degrees, and in the other direction, about 8 degrees. Accordingly, the outer jaw 110 is configured to pivot in the longitudinal direction relative to the binding post 114 up to about 28 degrees. Of course other articulation ranges are within the scope of this disclosure. The different angles, curved, and flat surfaces can be seen in FIGS. 8B-D.

The central bore portion between the neck 286 and the outer clamp surface 278 is arranged and shaped to permit articulation relative to the binding post 114 in a manner that permits the inner clamp surface 278 to pivot and face the inner clamp surface 240 of the inner jaw 108. Here, the central bore 282 widens from the neck 286 toward the outer clamp surface 278. As can be seen in FIG. 8D, the central bore portion between the neck 286 and the outer clamp surface 278 is nonsymmetrical. In addition, the inner walls are formed with concave curves 287 near the neck 286. These curves 287 are shaped to interface with the spherical washer 116 in FIG. 4 and provide an articulation surface for the outer jaw 110 to articulate relative to the spherical washer 116 as the outer jaw 110 displaces to open and close the clamp 102.

In use, the outer jaw 110 displaces relative to the binding post 114 in the lateral direction as the inner jaw 108 pivots with respect to the saddle base 106. In addition, the outer jaw 110 displaces relative to the inner jaw 108 to open the jaws to receive a bar into the transverse groove 280. This displacement is in the longitudinal direction, and as shown in FIGS. 4 and 8, the neck 286 of the central bore is shaped large enough to permit pivoting about the center of the concave curves longitudinally as well as laterally.

As shown in FIGS. 8B and 8C, the bias member grooves 285 extend longitudinally on each side of the central bore 282. These grooves extend from the transverse groove 280 rearwardly toward the rear end 274 and are sized and located to align with the bias member grooves 248 on the inner jaw 108. Together the bias member grooves 285 on the outer jaw 110 and the bias member grooves 248 on the inner jaw 108 receive the wire springs 122 (FIG. 5) which act between the two jaws 108, 110 to bias the outer jaw to an open, bar-receiving position. These grooves 285 on the outer jaw 110 include a securing feature 288 formed as an inwardly extending indentation shaped to receive an end of the wire springs 122, as shown in FIG. 5.

Referring now to FIG. 8D, the rear end 274 of the outer jaw 110 includes a locking interface 290 shaped to contact the release lever 112 to secure the outer jaw 110 in the open position, and shaped to release the outer jaw 110 to close to the provisionally locked position. This locking interface 290 extends obliquely relative to the inner clamp face 276 and the outer clamp surface 278 and includes a protruding edge 292 that acts as a catch for the release lever 112 when the clamp 102 is in the open position. Although shaped as a protrusion, in some embodiments, the edge 292 is an indentation or other catch.

Figure 9:
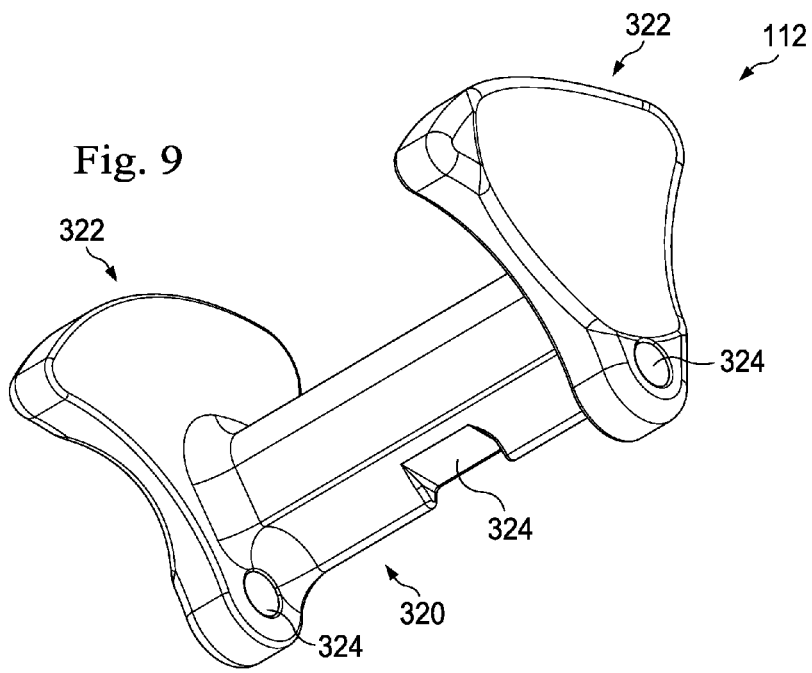
FIG. 9 is an illustration of a perspective view of a release lever according to the exemplary embodiment in FIG. 2.

FIG. 9 shows the release lever 112. In this exemplary embodiment, it includes a locking bar 320 extending between, and integrally formed with, grips 322. A pin receiving hole 324 in the grips 322 receives the pin 126 (FIG. 5), which extends parallel to the locking bar 320. The pin 126 also passes through the pivot portion 250 and the torsion spring 124 to pivotally secure the release lever 112 in place on the inner jaw 108.

As shown in FIG. 9 and in the cross sectional view of FIG. 4, the locking bar 320 includes a generally irregular quadrilateral cross-sectional shape, but also includes mild concave and convex curves. The curves may be concentric about a pivot axis formed by the pin 126 and the pin receiving holes 324. Accordingly, the curved surface may be concentric with the outer surface of the cylindrical pin 126.

The locking bar 320 may interface with the locking interface 290 on the outer jaw 110 to place the outer jaw 110 in the provisionally locked condition. Likewise, when pivoted about the pin 126, the locking bar 320 may interface with the rear end 274 of the outer jaw 110 to permit the outer jaw 110 to rest in the opened bar-receiving position.

Centrally disposed in the curved surface of the locking bar 320 is a cutout 324 facing the pin-receiving holes 324. This cutout 324 is sized to receive the torsion spring 124 as it extends about the pin 126. The torsion spring 124 applies a biasing force on the release lever 112 to place the release lever 112 in the provisionally locked position.

The grips 322 are ergonomically shaped for easy grasping with a thumb and forefinger. These are generally triangularly shaped and include protruding edges permitting a surgeon to grasp the release lever 112 with two fingers to pivot the release lever about the pin so that the outer jaw 110 moves to the open, bar-receiving position.

Figure 10A:
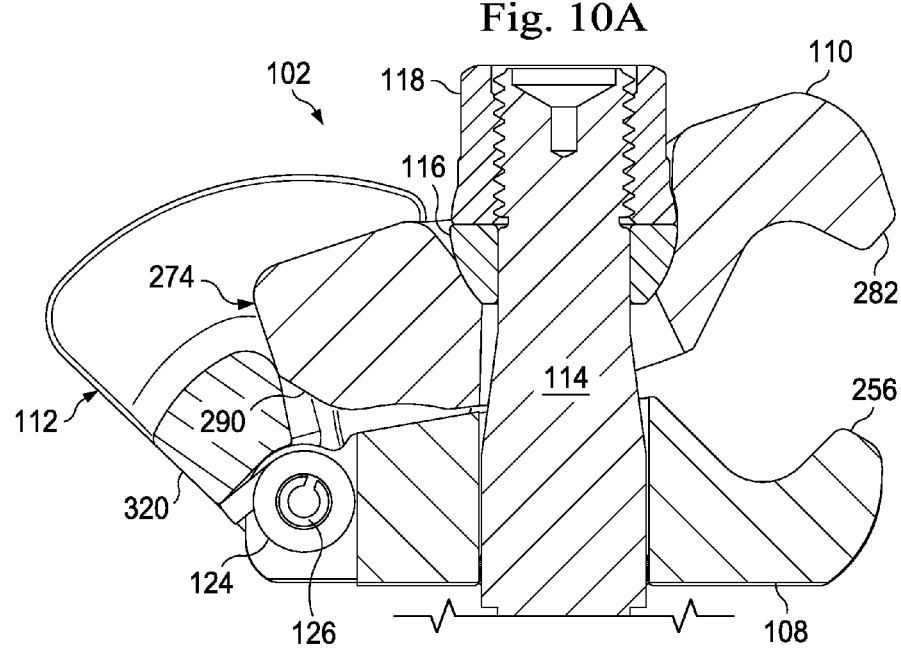
FIGS. 10A-C are a series of illustrations showing the clamping device of FIG. 2 changing from an open or bar-receiving condition to a provisionally locked condition.
Figure 10B:
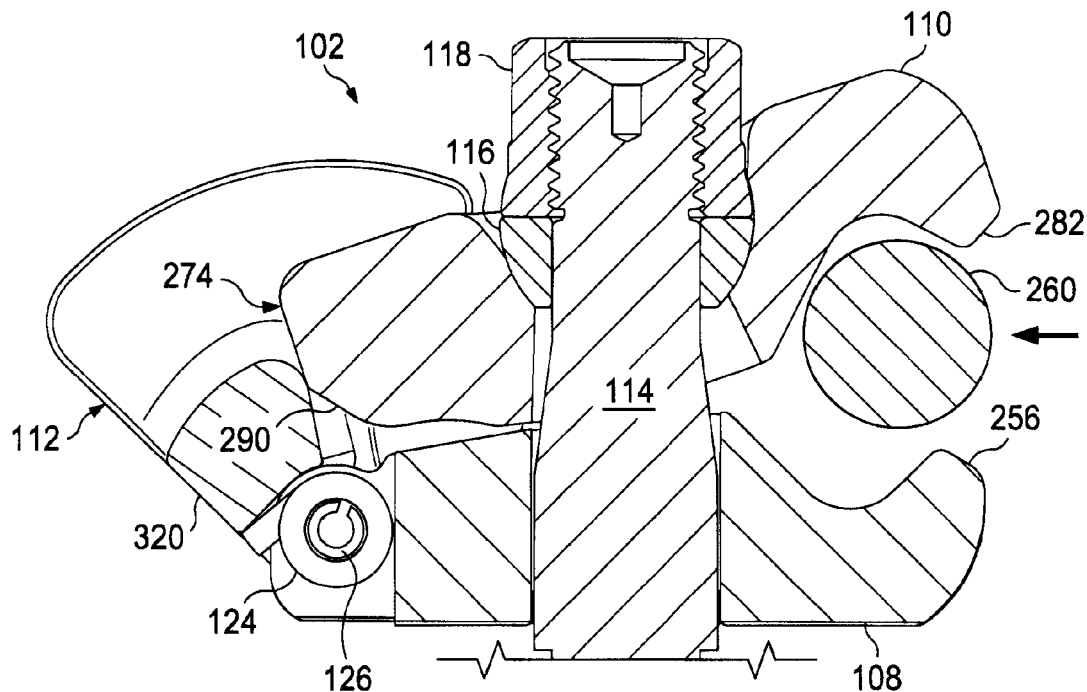
Figure 10C:
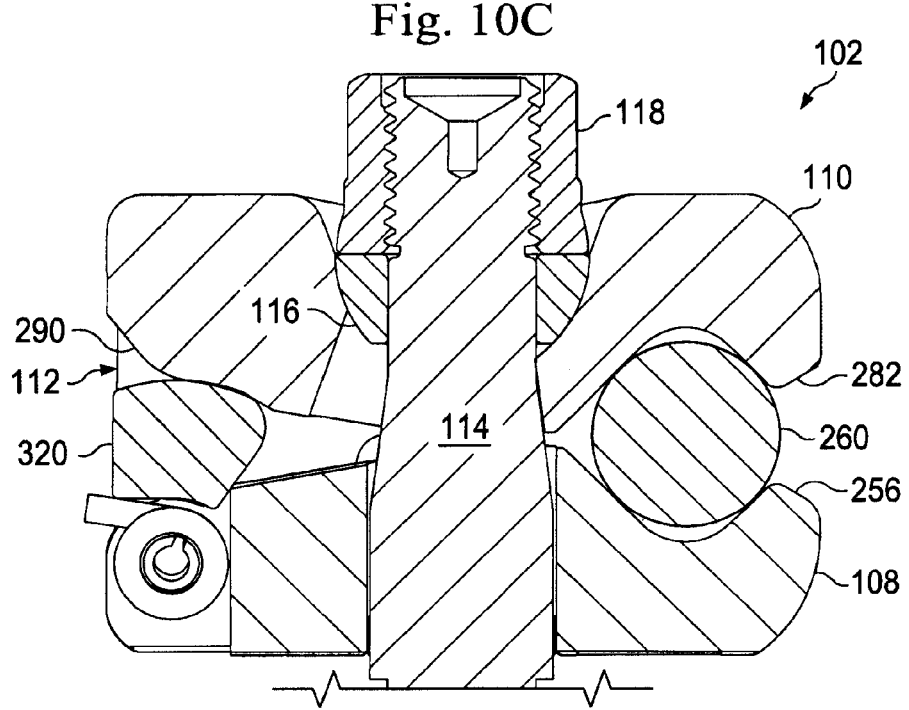

FIGS. 10A-C show the top clamp 102 in the open position, during bar insertion, and in the closed position, respectively. Referring first to FIG. 10A, in the open position, the release lever 112 is pivoted about the pivot connection so that the locking bar 320 lies behind the rear end 274 of the outer jaw 110.

In use, a surgeon may place the clamping device 100 in the open position by grasping the release lever 112 between his thumb and forefinger and pivoting the release lever 112 about the pin 126 to overcome the force of the biasing torsion spring 124. Once sufficiently drawn back, the wire spring (not shown in FIG. 10A) biases the outer jaw 110 to pivot about the spherical washer 116 to an open position, separating the outer jaw and inner jaw hook portions 282, 256. Accordingly, the shape and loading articulates the top jaw 110 to open the front end of the clamp 102. Accordingly, here, the device 100 is in a cocked position.

FIG. 10B shows a bar 260 being inserted between the inner and outer jaws 108, 110. As the bar contacts the rearward portion of the transverse groove 280 of the outer jaw 110, the outer jaw 110 is forced rearwardly. This rearward movement pivots the outer jaw about the spherical washer 116 enough to raise the rear end of the outer jaw 110 above the locking bar 320. Once this occurs, the biasing force of the torsion spring 124 pivots the release lever 112 so that the locking bar 320 acts against the locking interface surface 290 of the outer jaw 110. The torsion spring force overcomes the biasing force of the wire springs and as the release lever 112 continues to pivot, the locking bar 320 continues to force the outer jaw 110 further closed, thereby snapping shut to grip the bar 260.

FIG. 10C shows the clamp 102 in the provisionally closed position. In this position, the bar 260 is provisionally secured within the clamp 102 between the outer and inner jaws 110, 108. In this position, the bar 260 may be rotated within the clamp 102 or the clamp may be rotated about the bar, the clamp 102 may be slid along the bar 260, and the outer and inner jaws 110, 108 may be pivoted relative to the saddle base 106 and rotated about the binding post 114. Thus, the clamp 102 snaps onto a bar but permits continued adjustment as the surgeon finishes locating the pins or building the frame.

Once the pins and bars are in a desired position, and with reference to FIG. 4, the surgeon locks the clamp 102 against further movement by tightening one or both of the nuts 118 on the binding post 114. As discussed above, the use of a collar or snap ring on the binding post 114 may allow independent locking of both clamps 102, 104. This compresses the wave spring 120 and the radially extending splines in the opposing saddle bases 106 engage each other. This also meshes the splines on the inner jaw 108 and the concave side of the saddle base 106, as well as drives the spherical washer 116 tight against the outer jaw 110. The outer jaw 110 then is forced against the inner jaw 108 and the release lever 112 to more tightly secure the bar in place between the jaws. Thus, in a fully locked state, the clamping device 100 is locked against all relative movement of the clamps, including releasing the bar.

To release the bar, the surgeon performs the steps in reverse. Particularly, he first loosens the nuts, placing the clamping device 100 in the provisionally locked state. Then he may grasp and rotate the release lever 112 so that the locking bar 320 is out of engagement with the outer jaw 110. The outer jaw 110 will open and the bar may be removed. Or course, if the clamps 102, 104 are independent lockable, such as when a snap ring or collar is incorporated into the binding post 114, then the clamps may be locked or released independently.

FIGS. 11-15 show another embodiment of a clamping device, referred to herein as 400. The device 400 is a low-profile clamping device that, like the device 100 discussed above, minimizes the pin to bar centerline distance. Large centerline distances increase the working envelope and increase the moment arm of the clamping device, subjecting the clamping device to increased moment loading necessitating a larger device. The devices shown herein, including the exemplary device in FIGS. 11-15, minimizes the pin to bar centerline distance by replacing the ball joint with two cylindrical surfaces on the inner jaw halves (one for each clamp half) and retaining a revolute joint between the two clamp assemblies so that it achieves the roll, pitch and yaw of a ball joint while also adding two additional degrees a freedom, namely the ability for the jaw halves to translate along the cylinder axes allowing for greater ease of assembly, fracture reduction, and load sharing while maintaining a close pin to bar centerline distance resulting in a more compact, lower loaded device.

Added degrees of freedom can be appreciated by considering a simply supported beam. A beam with two simple supports can be described and analyzed with simple means; however skeletal fixation does not rely on simple supports but rather fixed ones. In this condition a misalignment or variations in stiffness of one support relative to the other results in an unequal sharing of the loads, or rather, an indeterminate problem. This is further complicated by the fact that at a minimum there are typically at least four pins for each bar, if the pins are considered the supports and the bar the beam it can be readily appreciated why additional degrees of freedom are advantageous.

Figure 11:
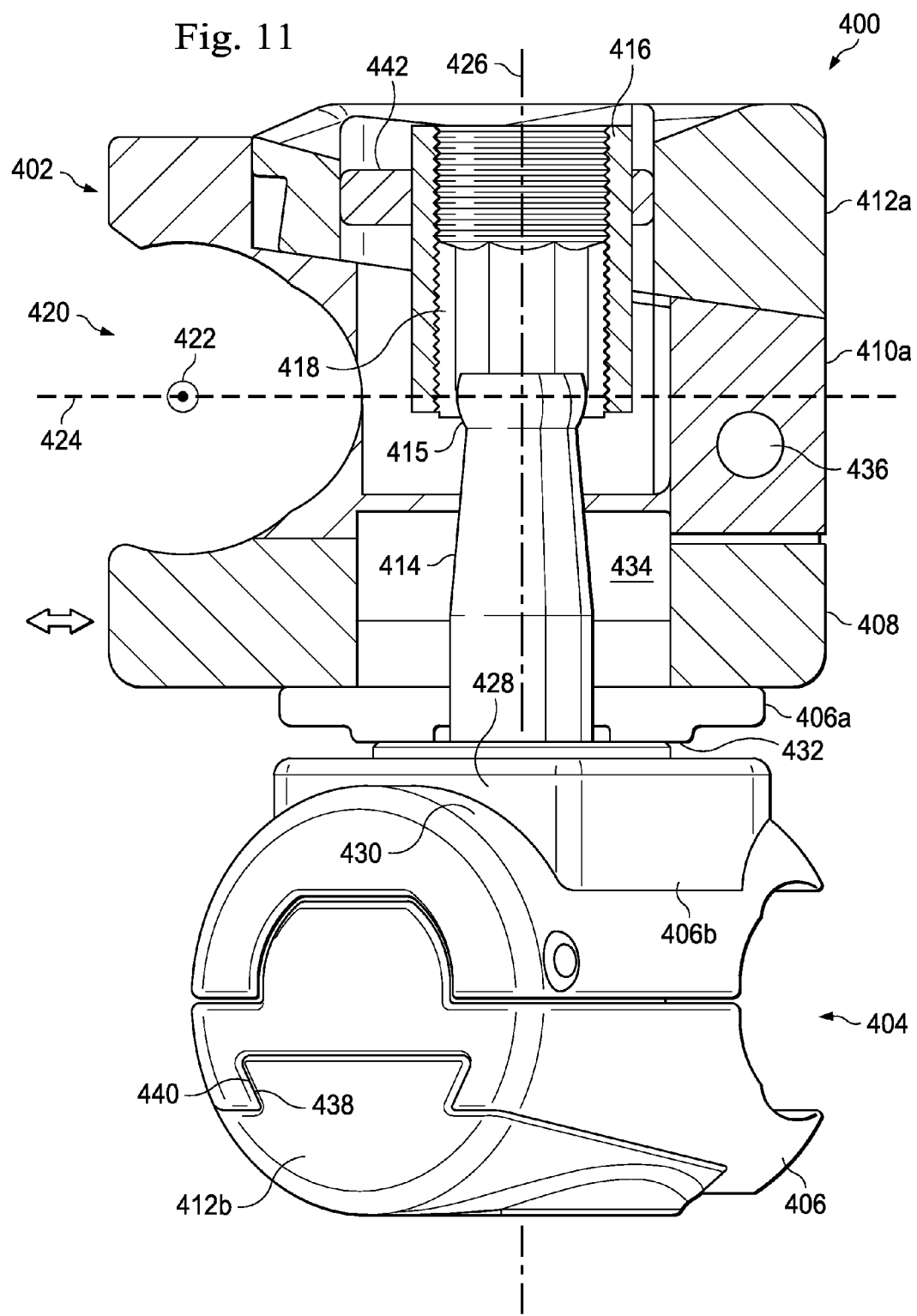
FIG. 11 is an illustration of a partial cross-sectional view of a clamping device according to one exemplary embodiment of the present disclosure.

Turning now to FIG. 11, the exemplary clamping device 400 includes both a top clamp 402 as a bar clamp and a bottom clamp 404 as a pin clamp. In some embodiments, the top and bottom clamps 402, 404 each operate in an identical manner and differ only in the size of the cylinder that the pin and bar clamp can accommodate. Like the top and bottom clamps 102, 104 discussed above, the clamp pair 402, 404 can be used to fixate pins to pins, pins to bars, or bars to bars or a single clamp can be used to fixate either a pin or a bar to some other apparatus such as a ring or monolateral external fixation and/or deformity correction device. The clamp mechanism whether used singly or in pairs operates the same as each half is independent of one another.

FIG. 11 shows the top clamp 402 in cross-section and the clamp 404 as a solid view. Each clamp 402, 404 includes a saddle base 406, an inner jaw 408, an outer jaw 410, and a release slide 412. These are connected together by a binding post 414, a compression sleeve 416, and a tightening nut 418. The inner and outer jaw 408, 410 cooperate to form an opening 420 for receiving a bar therein.

Each clamp 402, 404 of the clamping device 400 provides multiple degrees of freedom. FIG. 11 shows the degrees of freedom as a roll axis 422, a pitch axis 424, and a yaw axis 426 in the upper clamp 402. The roll axis 422 is the axis of a bar within the clamp 402 and about which the clamping device 400 rotates. The pitch axis 424 is the axis about which the outer and inner jaws 410, 408 rotate relative to the saddle base 406 and relative to the lower clamp 404. The yaw axis 426 is defined by the binding post 414 and about which one of clamps 402, 404 can rotate relative to the other. As can be seen in FIG. 4, the two pitch axes 152 are offset from each other and lie in parallel planes. Offsetting the axes in this way assists in lowering the overall profile of the device 100. In some embodiments, these may be offset a distance within the range of about 0.2 inch or greater. Other embodiments may have the axes offset more than 0.5 inch. Yet others have the axes offset more or less than these exemplary distances.

The binding post 414 secures the top and bottom clamps 402, 404 together, or in other embodiments, secures one of the clamps to another fixation or other device. The view in FIG. 11 shows only one half of the binding post 414, as the other half extends into the bottom clamp 404. The binding post axis corresponds to the yaw axis 426, about which the clamps 402, 404 can rotate relative to each other and relative to the binding post 414.

At its upper end, the binding post 414 includes a spherical ball joint 415. The center of this spherical joint 415 coincides with both the yaw axis 426 and the pitch axis 424 of the cylindrical surface of the base 406 described below. This relationship allows the clamp 402, as well as any pin or bar contained within the clamp 402 to pivot about its center and rotate about the pitch axis 424.

The base 406a of the upper clamp 402 includes a concave saddle portion 428 that interfaces with the lower outer surface 430 the inner jaw 408. The concave saddle portion 428 has an axis corresponding to the pitch axis 424, and about which the inner jaw 408, the outer jaw 410, and the release slide 412 can rotate.

Like the exemplary clamping device 100 discussed above, the base 406a has a circular array of radial splines on its bottom surface 432 that act to mate with radial splines on the corresponding base 406b on the lower clamp assembly 404 or some other foundation if used individually. Similar to those splines described above, the splines resemble those on a poker chip and provide positive retention from planar rotation when the bottom surfaces 432 are clamped together. The concave saddle portion 428 side of the base 406a is a cylindrical surface which in some embodiments, has a series of longitudinal splines as shown and discussed above with reference to the clamping device 100. These longitudinal splines mate to similar splines on the bottom surface 430 of the inner jaw 408 and act to provide positive rotation retention when in the clamped or locked state.

The lower or inner jaw 408 is cylindrically shaped on its lower surface 430 and includes longitudinal splines that interdigitate with those on the base 406a when in the clamped state. The longitudinal splines may be similar to those shown in and described with reference to FIGS. 7A, 7C and 7D. A transverse groove formed in the inner jaw 408 in part creates the opening 420 that accepts the pin or bar. In addition, the inner jaw 408 includes a central clearance bore 434 or hole through which the binding post extends. This central bore 434 is sized and configured to provide clearance to the binding post 414 that allows for both rotation about the pitch axis 424 in the amount of, for example, ±20 degrees as well as axial translation along the pitch axis 424 as indicated by the arrow shown. The amount of axial translation may be limited by the size of the binding post and the size of the central bore 434. In some embodiments, the permitted axial translation is within a range of 0.1 to 1 inch. When both clamps 402, 402 translate, the total amount of translation for the device 400 can be up to double this range.

A hinge pin 436 connects the inner jaw 408 and the outer jaw 410. In the embodiment shown, the inner jaw 408 includes a recess into which a portion of the outer jaw extends. The hinge pin 436 passes through both the inner jaw and the outer jaw providing a pivot hinge connection that permits the outer and inner jaws 408, 410 to be opened and closed to achieve sufficient clearance at the opening 420 to receive a bar or pin.

Like the inner jaw 408, the outer jaw 410 half has a transverse cut (not shown) that accepts the pin or bar. The outer jaw includes a dovetail slot 430 that accepts the release slide 412, and allows it to slide relative to the outer jaw 410.

The release slide 412 cooperates with the outer jaw 410 to either open or close the opening 430. It has a corresponding dovetail feature 440 which mates with the dovetail slot on the outer jaw 410. Because this dovetail slot 438 on the outer jaw 410 is on a slope, when the release slide 412 is slid rearward it also moves downward, removing the constraint on the outer jaw 410 and allowing the outer jaw 410 to open in order to accept the pin or bar. Once the release slide 412 is slid back up the ramp it acts as a door stop in preventing the outer jaw 410 from opening up, preventing the inadvertent release of the pin or bar. Some embodiments include a compression spring or other biasing member that biases the release slide 412 into the upper locked position.

Figure 16:
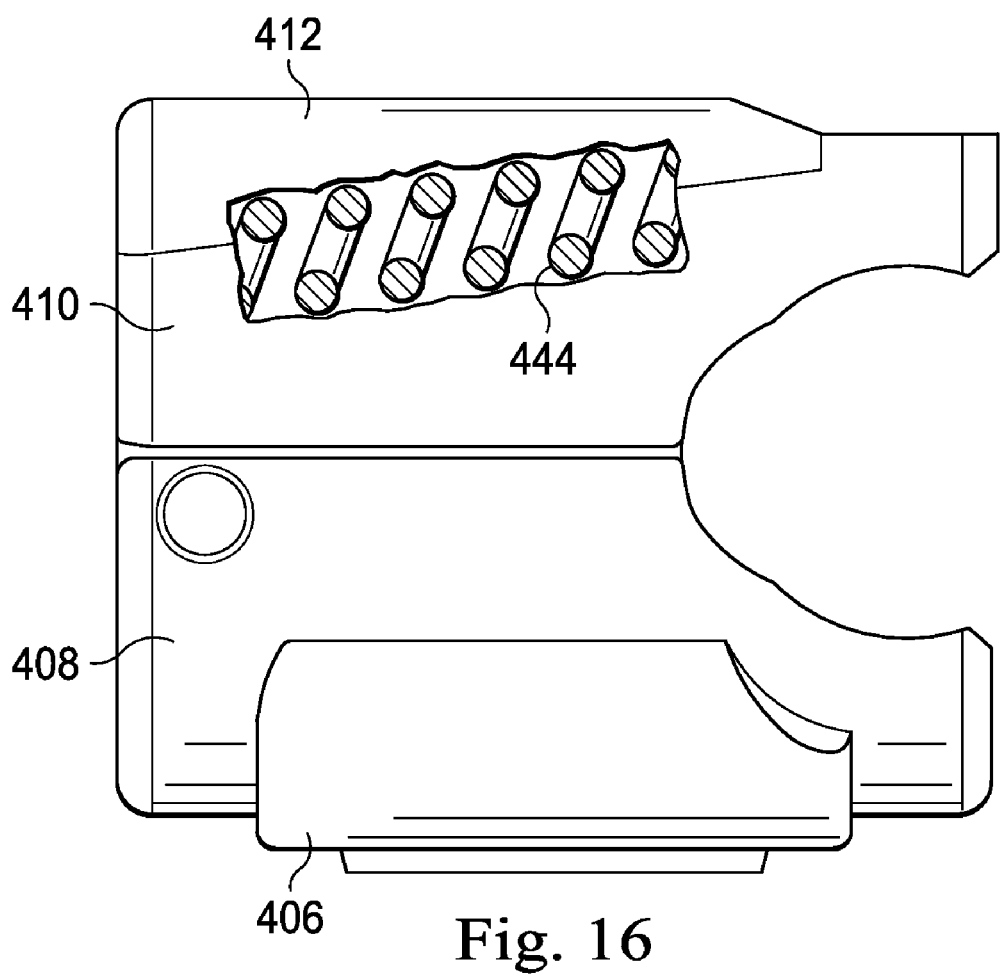
FIG. 16 is an illustration of a partial cross-sectional view of an exemplary clamping component making up a portion of the clamping device according to another exemplary embodiment of the device in FIG. 11.

FIG. 16 for example, shows a partial cross-sectional view of the clamp 402 with an exemplary biasing member 444 that applies loading to bias the release slide 412 into the locked position. Here, the biasing member is disposed half in the upper jaw 410 and half in the release slide 412. Although shown as a coil spring, other biasing members are contemplated.

Figure 14:
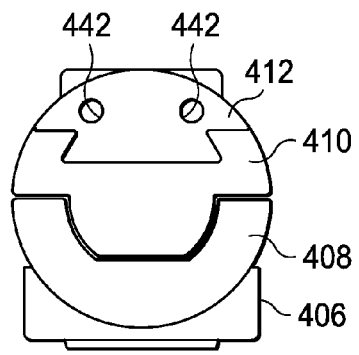
FIG. 14 is an illustration of a back view of an exemplary clamping component making up a portion of the clamping device according to the exemplary embodiment in FIG. 11.
Figure 12:
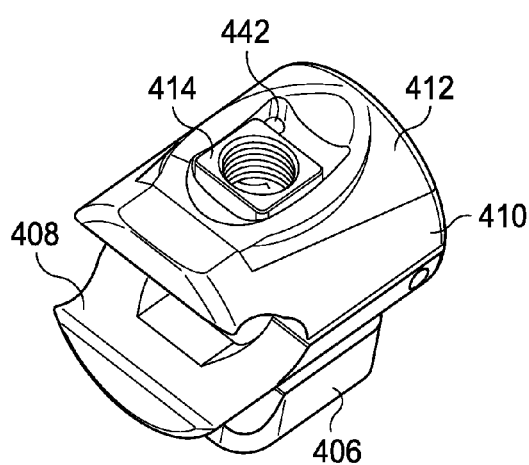
FIG. 12 is an illustration of a perspective view of an exemplary clamping component making up a portion of the clamping device according to the exemplary embodiment in FIG. 11.

Referring to FIG. 11, one or more guide pins 442 extends through the release slide 412 and across the central clearance bore 434. As shown in FIG. 14, these guide pins 442 may be introduced through a rear portion of the release lever. The guide pins pass through receiving bores (not shown) on compression sleeve 416 securing the compression sleeve to the release slide 412. During translation as well as during actuation of the release lever, the guide pines 412 slide relative to the compression sleeve 416.

Figure 15:
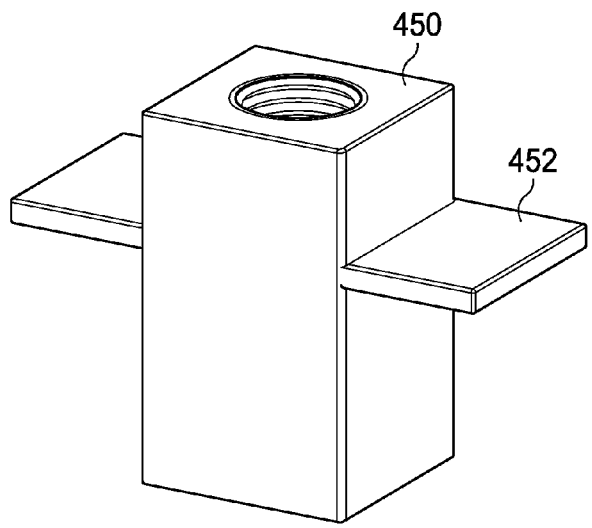
FIG. 15 is an illustration of a perspective view of an exemplary sleeve forming a portion of the clamping device according to the exemplary embodiment in FIG. 11.
Figure 13:
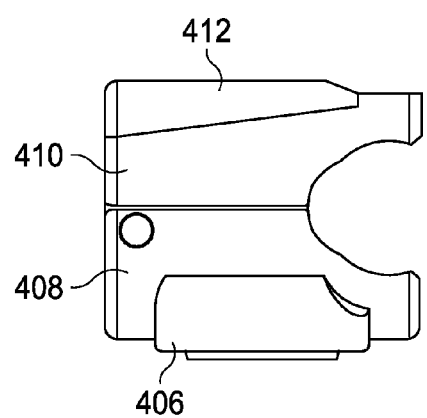
FIG. 13 is an illustration of a side view of an exemplary clamping component making up a portion of the clamping device according to the exemplary embodiment in FIG. 11.

In another exemplary embodiment, instead of employing guide pins to secure the compression sleeve in the bore of the release slide, the compression sleeve itself includes extending protrusions that fit into and slide within guide slots formed inside the release slide bore. One exemplary embodiment of such a compression sleeve 450 is shown in FIG. 15. The compression sleeve 450 includes wings 452 protruding from opposing sides that fit within a guide slot formed in the bore sidewall of the release slide 412, securing the compression sleeve 416 to the release slide 412. The wings allow the compression sleeve 416 to slide front to back with respect to the release slide 412, but does not allow it to move up and down relative to the release slide 412. On the inner cylindrical bore is a left hand helical thread that engages with the tightening nut 418.

The tightening nut 418 engages with the compression sleeve 416 on its outer threaded cylindrical surface. It includes at its lower end a spherical joint that mates with the binding post 414, through its center is a broached hexagonal hole that accepts a tool for tightening.

In use, a surgeon may slide back the release slide 412 relative to the outer jaw 410. This opens the outer jaw 410 relative to the inner jaw 408. Once a bar or pin is in the transverse cuts between the outer and inner jaws 410, 408, the release slide 412 may be either moved, or snapped back toward the front of outer jaw 410. This closes the jaw positively retaining the pin or bar from detachment but not firmly fixating it. Accordingly this is a provisionally locked position, allowing the pin or bar to move in accordance with the degrees of freedom of the clamping device 400.

Tightening the tightening nut 418 provides a clamping force between the binding post 414 and the release slide 412 effectively clamping together the base 406, the outer and inner jaws 408, 410, and the release slide 412, and applying pressure to the pin or bar in the clamp. Because of the slight slope between the outer jaw 410 and the release slide 412, the release slide 412 acts as a door stop on the outer jaw 410. Thus, the greater the clamping force the greater the resistance to sliding thus preventing the jaws from opening. Releasing the pin may be accomplished by reversing the steps.

In some aspects this disclosure is directed to an exemplary clamping device for an external fixation system. The device includes a first clamping system connected to a second clamping system by a saddle assembly. The saddle assembly includes first and second outwardly facing concave surfaces that respectively interface with the first and second clamping systems. The first and second outwardly facing concave surfaces have a respective first and a second pitch axis. The first clamping system is moveable relative to saddle assembly to pivot within a range of more than 20 degrees about the first pitch axis and the second clamping system moveable relative to saddle assembly to pivot within a range of more than 20 degrees about the second pitch axis. In some examples, the first and second pitch axes are offset by more than 0.5 inch. In some examples, the first and second pitch axes lie in parallel planes. In some examples, the first and second clamping system are respectively moveable relative to saddle assembly to pivot within a range of 40 degrees or more about the first and second pitch axes, respectively.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

I claim:

1. A clamping device for an external fixation system, comprising:
   a first clamping system, a second clamping system, and a post component extending into the first and second clamping system;
   the first clamping system comprising
      a first outer jaw;
      a first inner jaw having an inner surface facing the outer jaw, the outer and inner jaws together forming an opening for receiving a first fixation element of the external fixation system, the first inner jaw including a substantially cylindrical outer clamp surface having splines formed thereon; and
      a first base component having a concave surface interfacing with the first inner jaw and an opposing bottom facing surface, the concave surface of the first base component including splines thereon, the splines of the first inner jaw interdigitating with the splines of the first base component;
   the second clamping system comprising
      a second outer jaw;
      a second inner jaw having an inner surface facing the second outer jaw, the second outer and second inner jaws together forming a second opening for receiving a second fixation element of the external fixation system; and
      a second base component having a concave surface interfacing with the second inner jaw and an opposing bottom facing surface,
      the concave surface of the first base component facing away from the concave surface of the second base component, and the opposing bottom facing surface of the first component being in selective engagement with the opposing bottom facing surface of the second component.

2. The clamping device of claim 1, further including a bias member biasing the first outer and first inner jaw to an open bar-receiving position.

3. The clamping device of claim 1, wherein the first inner jaw includes a central bore formed therein, the central bore receiving the post component and being shaped to permit articulation relative to the post component in a transverse direction and being shaped to substantially limit articulation relative to the post component in a longitudinal direction.

4. The clamping device of claim 3, wherein the first outer jaw includes a non-symmetrical central bore, the central bore formed therein, the central bore receiving the post component and being shaped to permit a first amount of articulation relative to the post component in a transverse direction and being shaped to permit a second amount of articulation relative to the post component in a longitudinal direction, the amount of permitted articulation in the transverse direction being greater than the amount of permitted articulation in the longitudinal direction.

5. The clamping device of claim 1, comprising a trigger system that releases the first outer and first inner jaw from an open bar-receiving condition to a provisionally locked condition.

6. The clamping device of claim 5, wherein the trigger system comprises a release component and a biasing element that biases the release component toward the provisionally locked condition.

7. The clamping device of claim 6, wherein the release component includes first and second grasping elements connected by a transversely extending bar that interfaces with a biasing element and with the outer jaw.

8. The clamping device of claim 5, wherein the trigger system comprises a release component attached to the first inner jaw, the release component slidingly engaging the first outer jaw to bias the outer jaw to the provisionally locked condition.

9. The clamping device of claim 1, including a tightening component configured to simultaneously compress the first and second clamping systems to securely place the first and second clamping systems in a locked condition.

10. The clamping device of claim 9, wherein the tightening component is a first tightening component associated with the first clamping system, the clamping device further comprising a second tightening component associated with the second clamping system, wherein each of the first and second tightening components are configured such that either tightening component will simultaneously compress the first and second clamping systems to securely place the first and second clamping systems in a locked condition.

11. The clamping device of claim 1, including a spherical portion disposed about the post component, the spherical portion interfacing with the first outer jaw and facing toward the first base member.

12. The clamping device of claim 1, wherein the concave surface of the base component has an axis, and wherein the first inner jaw includes a central bore sized to permit axial translation of the inner jaw along the axis.

13. The clamping device of claim 1, comprising a release slide having an angled surface that interfaces with an angled surface of the first outer jaw, such that translational movement of the release slide in a first direction permits the outer jaw to open and such that translational movement of the release slide in an opposing direction forces the outer jaw to a provisionally locked condition.

14. A clamping device for an external fixation system, comprising:
a post component having a yaw axis,
a first clamping system secured to the post component and rotatable about the yaw axis, the first clamping system comprising
a first outer jaw;
a first inner jaw having an inner surface facing the outer jaw, the first outer and first inner jaws together forming an opening for receiving a first fixation element of the external fixation system, the first inner jaw and first outer jaw having a roll axis alignable with a longitudinal axis of the fixation element, the first clamping system and post component being rotatable about the roll axis, the first inner jaw also having a cylindrical outer-facing surface; and
a first base component having a cylindrical concave surface having a pitch axis, the concave surface of the first base component interfacing with the cylindrical outer-facing surface on the first inner jaw, the first outer and first inner jaws being rotatable relative to the first base component and the post component about the pitch axis;
a second clamping system secured to the post component and rotatable about the yaw axis, the second clamping system having a second outer jaw, a second inner jaw, and a second base component, the first base component having splines that selectively interdigitate with splines of the second base component; and
a bias member that biases the first and second base components away from each other.

15. The clamping device of claim 14, including a spherical portion disposed about the post component and interfacing with the first outer jaw, the first outer jaw being articulatable with respect to the spherical portion, the spherical portion having a center point, the pitch axis of the first base component passing through or near to the center point.

16. The clamping device of claim 14, wherein the first outer and first inner jaws are movable between an open bar-receiving position and a clamped, closed-position, the clamping device further comprising a bias member biasing the first outer and first inner jaw to an open bar-receiving position.

17. The clamping device of claim 14, wherein the first inner jaw includes a central bore formed therein, the central bore receiving the post component and being shaped to permit articulation relative to the post component in a transverse direction and being shaped to substantially limit articulation relative to the post component in a longitudinal direction.

18. The clamping device of claim 17, wherein the first outer jaw includes a non-symmetrical central bore, the central bore formed therein, the central bore receiving the post component and being shaped to permit a first amount of articulation relative to the post component in a transverse direction and being shaped to permit a second amount of articulation relative to the post component in a longitudinal direction, the amount of permitted articulation in the transverse direction being greater than the amount of permitted articulation in the longitudinal direction.

19. The clamping device of claim 14, comprising a trigger system that releases the first outer and first inner jaw from an open bar-receiving condition to a provisionally locked condition.

20. The clamping device of claim 19, wherein the trigger system comprises a release component and a biasing element that biases the release component toward the provisionally locked condition.

21. The clamping device of claim 20, wherein the release component includes first and second grasping elements connected by a transversely extending bar that interfaces with a biasing element and with the outer jaw.

22. The clamping device of claim 19, wherein the trigger system comprises a release component attached to the first inner jaw, the release component slidingly engaging the first outer jaw to bias the outer jaw to the provisionally locked condition.

23. The clamping device of claim 14, including a tightening component interfacing with the post component, the tightening component being configured to compress the first clamping system to securely place the first clamping system in a locked condition.

24. The clamping device of claim 14, including a spherical portion disposed about the post component, the spherical portion interfacing with the first outer jaw and facing toward the first base member.

25. The clamping device of claim 14, wherein the concave surface of the base component has an axis, and wherein the first inner jaw includes a central bore sized to permit axial translation of the inner jaw along the axis.

26. The clamping device of claim 14, comprising a release slide having an angled surface that interfaces with an angled surface of the first outer jaw, such that translational movement of the release slide in a first direction permits the outer jaw to open and such that translational movement of the release slide in an opposing direction forces the outer jaw to a provisionally locked condition.

27. The clamping device of claim 14, including a tightening component configured in a manner that an action of tightening the tightening component simultaneously locks both the first and second clamping systems.

28. The clamping device of claim 27, wherein the tightening component is a first tightening component associated with the first clamping system, the clamping device further comprising a second tightening component associated with the second clamping system, wherein each of the first and second tightening components are configured in a manner that an action of tightening one of the tightening components simultaneously locks both the first and second clamping systems.

29. A clamping device for an external fixation system, comprising:
   a post component having a yaw axis;
   a first clamping system secured to the post component and rotatable about the yaw axis, the first clamping system comprising
      a first outer jaw;
      a first inner jaw having an inner surface facing the outer jaw, the first outer and first inner jaws together forming an opening for receiving a first fixation element of the external fixation system, the first inner jaw and first outer jaw having a roll axis alignable with a longitudinal axis of the fixation element, the first clamping system and post component being rotatable about the roll axis, the first inner jaw also having a cylindrical outer-facing surface; and
      a first base component having a cylindrical concave surface having a pitch axis, the concave surface of the first base component interfacing with the cylindrical outer-facing surface on the first inner jaw, the first outer and first inner jaws being rotatable relative to the first base component and the post component about the pitch axis
   wherein the cylindrical surface of the first inner jaw includes splines formed thereon, and
   wherein the cylindrical concave surface of the first base component includes splines thereon, the splines of the first inner jaw interdigitating with the splines of the first base component.

30. The clamping device of claim 29, wherein the first outer and first inner jaws are movable between an open bar-receiving position and a clamped, closed-position, the clamping device further comprising a bias member biasing the first outer and first inner jaw to an open bar-receiving position.

31. The clamping device of claim 29, wherein the first inner jaw includes a central bore formed therein, the central bore receiving the post component and being shaped to permit articulation relative to the post component in a transverse direction and being shaped to substantially limit articulation relative to the post component in a longitudinal direction.

32. The clamping device of claim 31, wherein the first outer jaw includes a non-symmetrical central bore, the central bore formed therein, the central bore receiving the post component and being shaped to permit a first amount of articulation relative to the post component in a transverse direction and being shaped to permit a second amount of articulation relative to the post component in a longitudinal direction, the amount of permitted articulation in the transverse direction being greater than the amount of permitted articulation in the longitudinal direction.

33. The clamping device of claim 29, comprising a trigger system that releases the first outer and first inner jaw from an open bar-receiving condition to a provisionally locked condition.

34. The clamping device of claim 33, wherein the trigger system comprises a release component and a biasing element that biases the release component toward the provisionally locked condition.

35. The clamping device of claim 34, wherein the release component includes first and second grasping elements connected by a transversely extending bar that interfaces with a biasing element and with the outer jaw.

36. The clamping device of claim 33, wherein the trigger system comprises a release component attached to the first inner jaw, the release component slidingly engaging the first outer jaw to bias the outer jaw to the provisionally locked condition.

37. The clamping device of claim 29, including a tightening component interfacing with the post component, the tightening component being configured to compress the first clamping system to securely place the first clamping system in a locked condition.

38. The clamping device of claim 29, including a spherical portion disposed about the post component, the spherical portion interfacing with the first outer jaw and facing toward the first base member.

39. The clamping device of claim 29, wherein the concave surface of the base component has an axis, and wherein the first inner jaw includes a central bore sized to permit axial translation of the inner jaw along the axis.

40. The clamping device of claim 29, comprising a release slide having an angled surface that interfaces with an angled surface of the first outer jaw, such that translational movement of the release slide in a first direction permits the outer jaw to open and such that translational movement of the release slide in an opposing direction forces the outer jaw to a provisionally locked condition.

41. The clamping device of claim 29, comprising a second clamping system secured to the post component and rotatable about the yaw axis, the second clamping system having a second outer jaw, a second inner jaw, and a second base component, the first base component having splines that selectively interdigitate with splines of the second base component; and
   a bias member that biases the first and second base components away from each other.

* * * * *